United States Patent [19]

Goulait et al.

[11] Patent Number: 5,300,058

[45] Date of Patent: Apr. 5, 1994

[54] DISPOSABLE ABSORBENT ARTICLE HAVING AN IMPROVED MECHANICAL FASTENING SYSTEM

[75] Inventors: David J. K. Goulait; Dennis A. Thomas; Maureen E. Stanley, all of Cincinnati, Ohio

[73] Assignee: The Procter & Gamble Company, Cincinnati, Ohio

[21] Appl. No.: 988,541

[22] Filed: Dec. 10, 1992

[51] Int. Cl.$^5$ .............................................. A61F 13/15
[52] U.S. Cl. ..................................... 604/391; 24/448; 604/358
[58] Field of Search ........................ 604/358, 389–391; 24/448, 452

[56] References Cited

U.S. PATENT DOCUMENTS

| | | |
|---|---|---|
| 569,213 | 10/1896 | Lehnig . |
| 625,022 | 5/1899 | Crist . |
| 2,717,437 | 9/1955 | Mestral ................... 28/72 |
| 3,057,354 | 10/1962 | Roberts et al. . |
| 3,130,111 | 4/1964 | Izumi ..................... 161/48 |
| 3,147,528 | 9/1964 | Erb ........................ 24/204 |
| 3,397,697 | 8/1968 | Rickard . |
| 3,426,400 | 2/1969 | Lauro ..................... 24/255 |
| 3,461,513 | 8/1969 | Girard et al. ............ 24/204 |
| 3,536,518 | 10/1970 | Drelich .................. 117/38 |
| 3,550,223 | 12/1970 | Erb ........................ 24/204 |
| 3,557,407 | 1/1971 | Lemelson ................. 425/71 |
| 3,562,044 | 2/1972 | Erb ........................ 156/155 |
| 3,594,863 | 7/1971 | Erb .......................... 18/5 |
| 3,594,865 | 7/1971 | Erb .......................... 18/5 |
| 3,629,032 | 12/1971 | Erb ........................ 156/196 |
| 3,643,316 | 2/1972 | Girard et al. ........... 29/400 |
| 3,708,382 | 1/1973 | Erb ........................ 161/48 |
| 3,943,981 | 3/1976 | De Brabander ........... 139/391 |
| 4,056,593 | 11/1977 | de Navas Albareda ...... 264/145 |
| 4,169,303 | 10/1979 | Lemelson ................. 24/204 |
| 4,198,734 | 4/1980 | Brumlik .................. 24/204 |
| 4,285,343 | 8/1981 | McNair . |
| 4,462,784 | 7/1984 | Russell .................. 425/223 |
| 4,532,157 | 7/1985 | Schmidt et al. ......... 427/262 |
| 4,562,099 | 12/1985 | Hichcliffe .............. 427/282 |
| 4,589,876 | 5/1986 | Van Tilbrug . |
| 4,608,047 | 8/1986 | Mattingly . |
| 4,672,893 | 6/1987 | Mammarella, Sr. ....... 101/170 |
| 4,687,478 | 8/1987 | Van Tilburg . |
| 4,699,622 | 10/1987 | Toussant et al. ........ 604/389 |

(List continued on next page.)

FOREIGN PATENT DOCUMENTS

| | | |
|---|---|---|
| 2027159 | 7/1991 | Canada . |
| 0276970 | 8/1988 | European Pat. Off. ......... 44/13/02 |
| 0325473A1 | 7/1989 | European Pat. Off. ......... 44/18/00 |
| 0353972 | 2/1990 | European Pat. Off. ......... 61/13/02 |
| 0381087 | 8/1990 | European Pat. Off. . |
| 0388681 | 9/1990 | European Pat. Off. . |
| 0476992A1 | 3/1992 | European Pat. Off. . |
| 0491347A1 | 6/1992 | European Pat. Off. ......... 61/13/62 |
| 1551245 | 12/1968 | France . |
| 2432108 | 12/1980 | France ..................... 3/16 |
| 55-137942 | 10/1980 | Japan . |
| WO87/06522 | 11/1987 | PCT Int'l Appl. . |
| 2233876A | 1/1991 | United Kingdom . |
| 2244910A | 12/1991 | United Kingdom . |

*Primary Examiner*—Randall L. Green
*Assistant Examiner*—Rob Clarke
*Attorney, Agent, or Firm*—Steven W. Miller; E. Kelly Linman; Jacobus C. Rasser

[57] ABSTRACT

The invention is an absorbent article such as a sanitary napkin, comprising a main body portion which is divided into a first half and a second half by a principle transverse centerline, and an oriented hook fastening material joined to the first half and second half of the main body portion. The oriented hook fastening material is oriented in a direction having a vector component perpendicular to the principle transverse centerline of the main body portion. In an alternate embodiment of the present invention, the disposable absorbent article will have side flaps joined to the main body portion and an oriented hook fastening material joined to the side flaps. In another alternate embodiment of the present invention, the disposable absorbent article will have a combination of a pressure sensitive adhesive and an oriented hook fastening material joined to the main body portion.

38 Claims, 13 Drawing Sheets

U.S. PATENT DOCUMENTS

| | | | |
|---|---|---|---|
| 4,725,221 | 2/1988 | Balnz | 425/575 |
| 4,776,068 | 10/1988 | Smirlock et al. | 24/442 |
| 4,794,028 | 12/1988 | Fischer | 428/100 |
| 4,846,815 | 7/1989 | Scripps . | |
| 4,869,724 | 9/1989 | Scripps . | |
| 4,876,982 | 10/1989 | Claassen . | |
| 4,894,060 | 1/1990 | Nestegard | 604/391 |
| 4,900,319 | 2/1990 | Richwine . | |
| 4,900,320 | 2/1990 | McCoy . | |
| 4,917,697 | 4/1990 | Osborn, III et al. . | |
| 4,938,835 | 7/1990 | Ludwig | 118/68 |
| 4,963,140 | 10/1990 | Robertson . | |
| 4,973,326 | 11/1990 | Wood et al. | 604/391 |
| 4,984,339 | 1/1991 | Provost et al. | 24/452 |
| 4,995,873 | 2/1991 | Knight | 604/391 |
| 5,019,065 | 5/1991 | Scripps . | |
| 5,040,275 | 8/1991 | Eckhardt et al. . | |
| 5,053,028 | 10/1991 | Zoia et al. . | |
| 5,058,247 | 10/1991 | Thomas et al. . | |
| 5,116,563 | 5/1992 | Thomas et al. | 156/66 |
| 5,122,219 | 6/1992 | Ludwig | 156/244.17 |
| 5,131,119 | 7/1992 | Murasaki et al. . | |
| 5,135,522 | 8/1992 | Fahrenkrug et al. . | |
| 5,180,534 | 1/1993 | Thomas et al. . | |

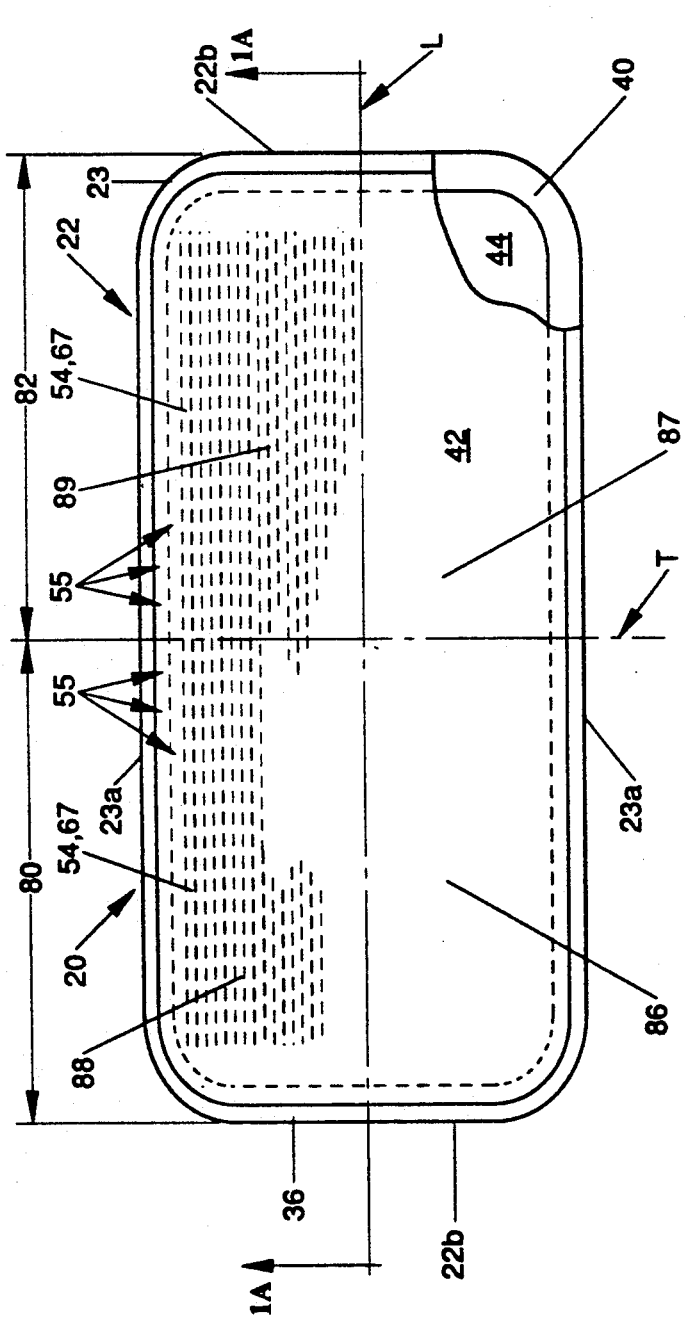
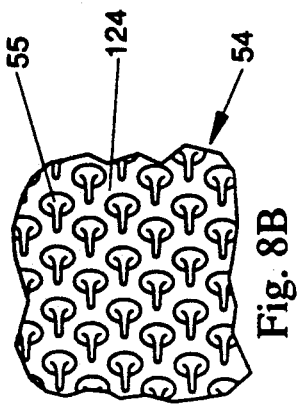
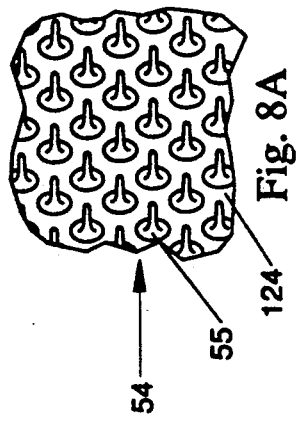
Fig. 1
Fig. 8A
Fig. 8B

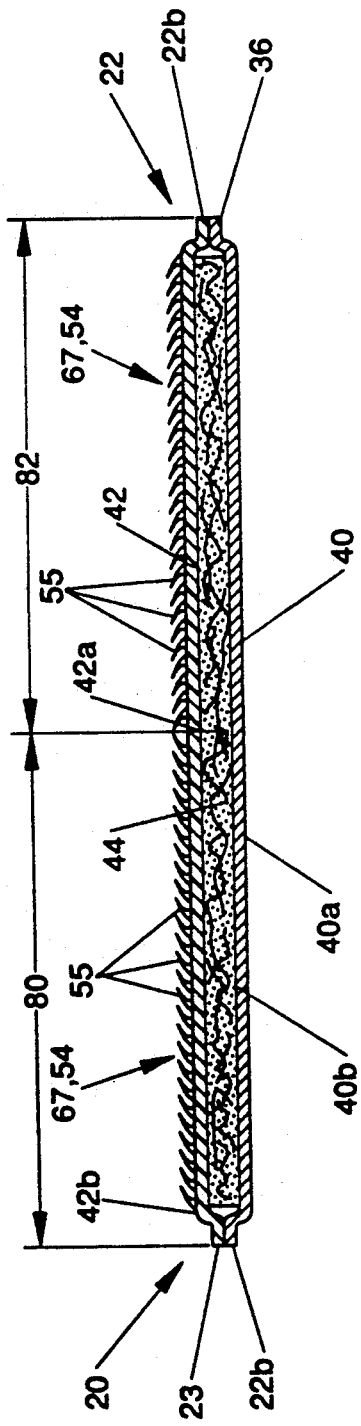
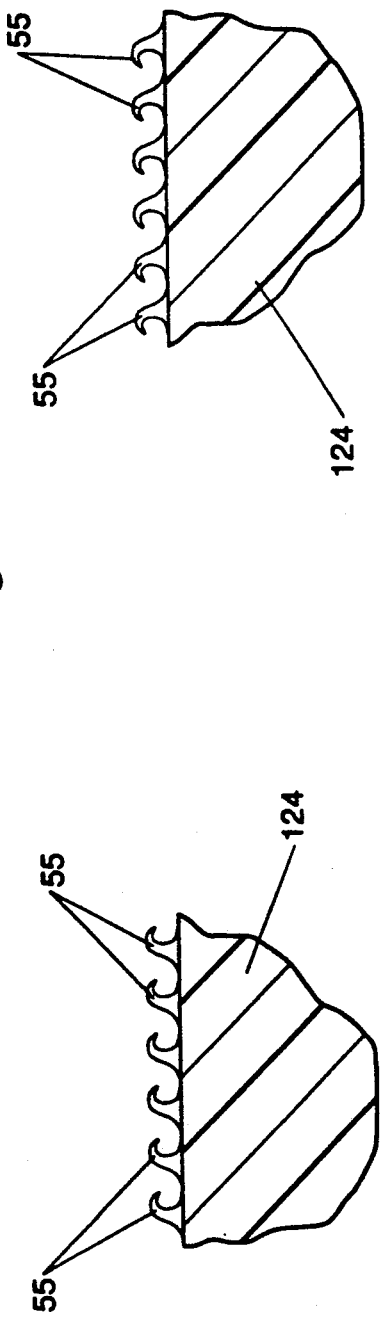

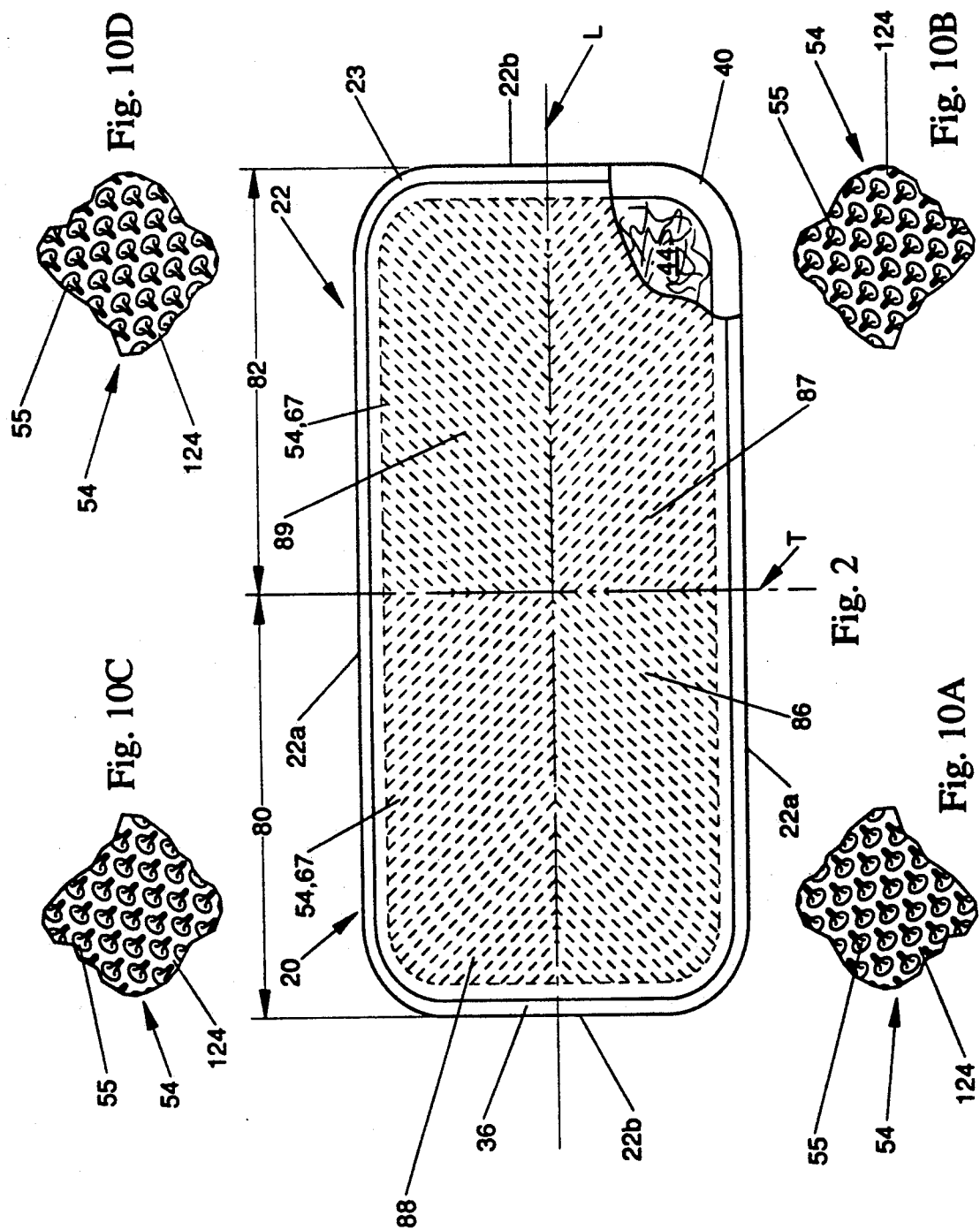

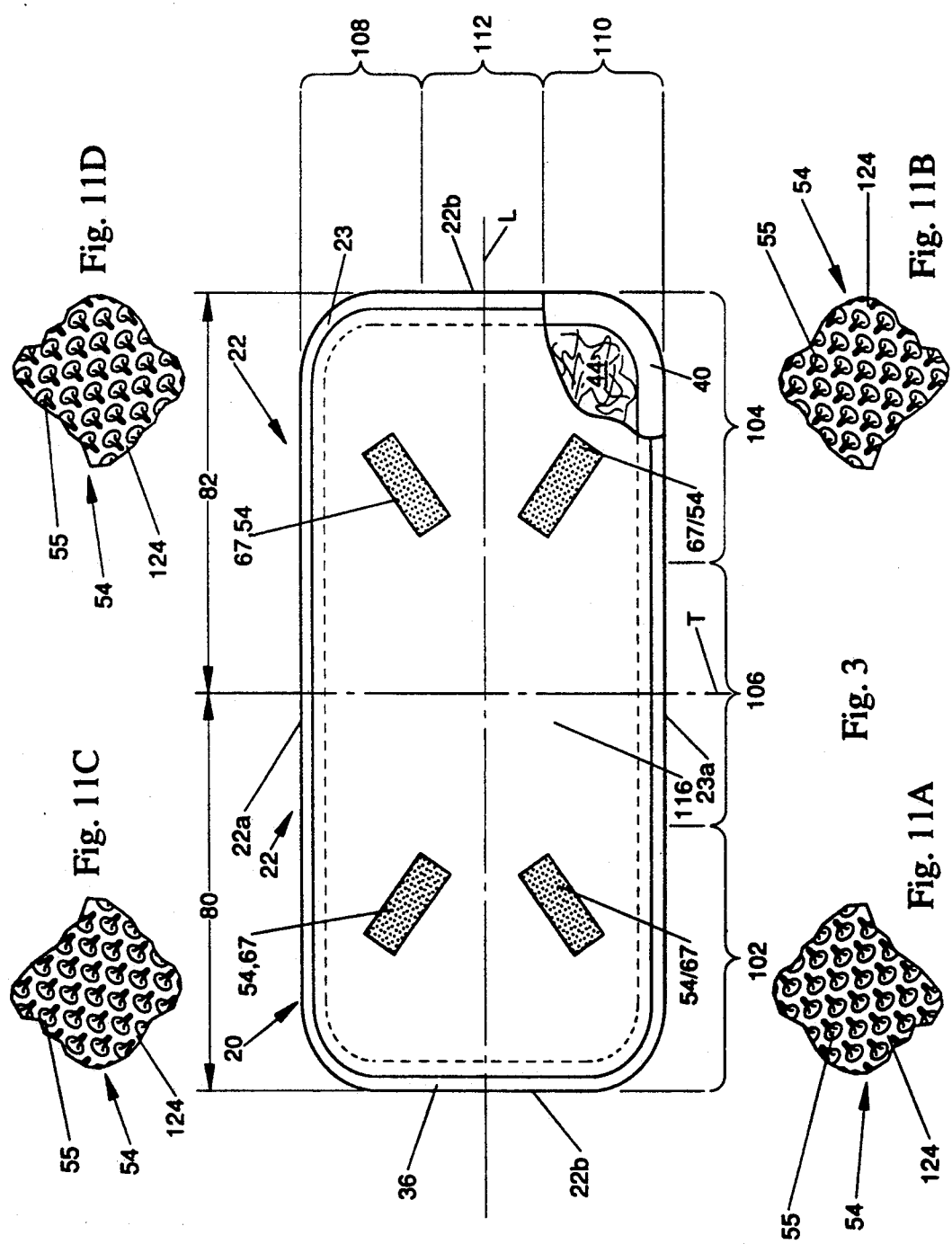

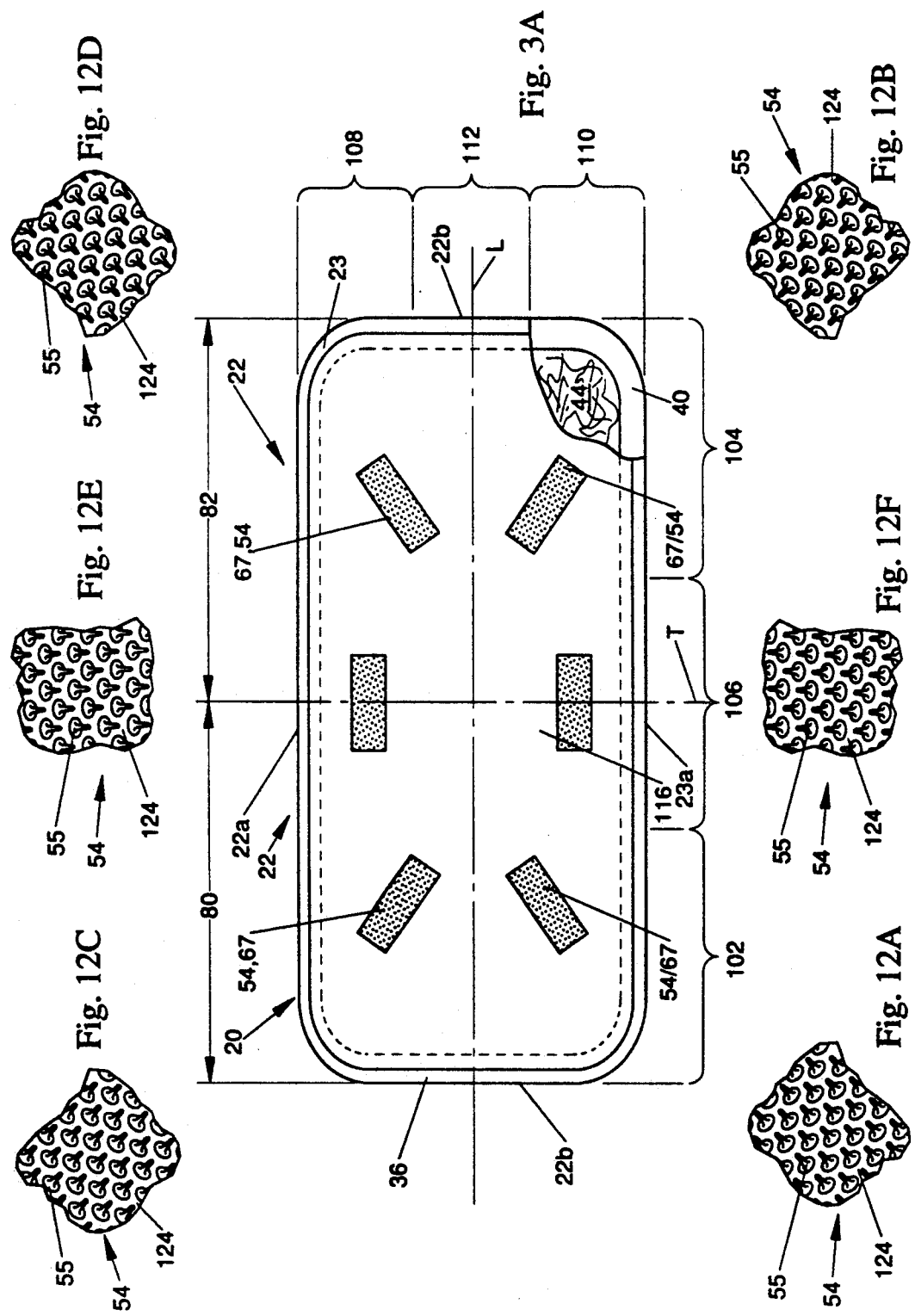

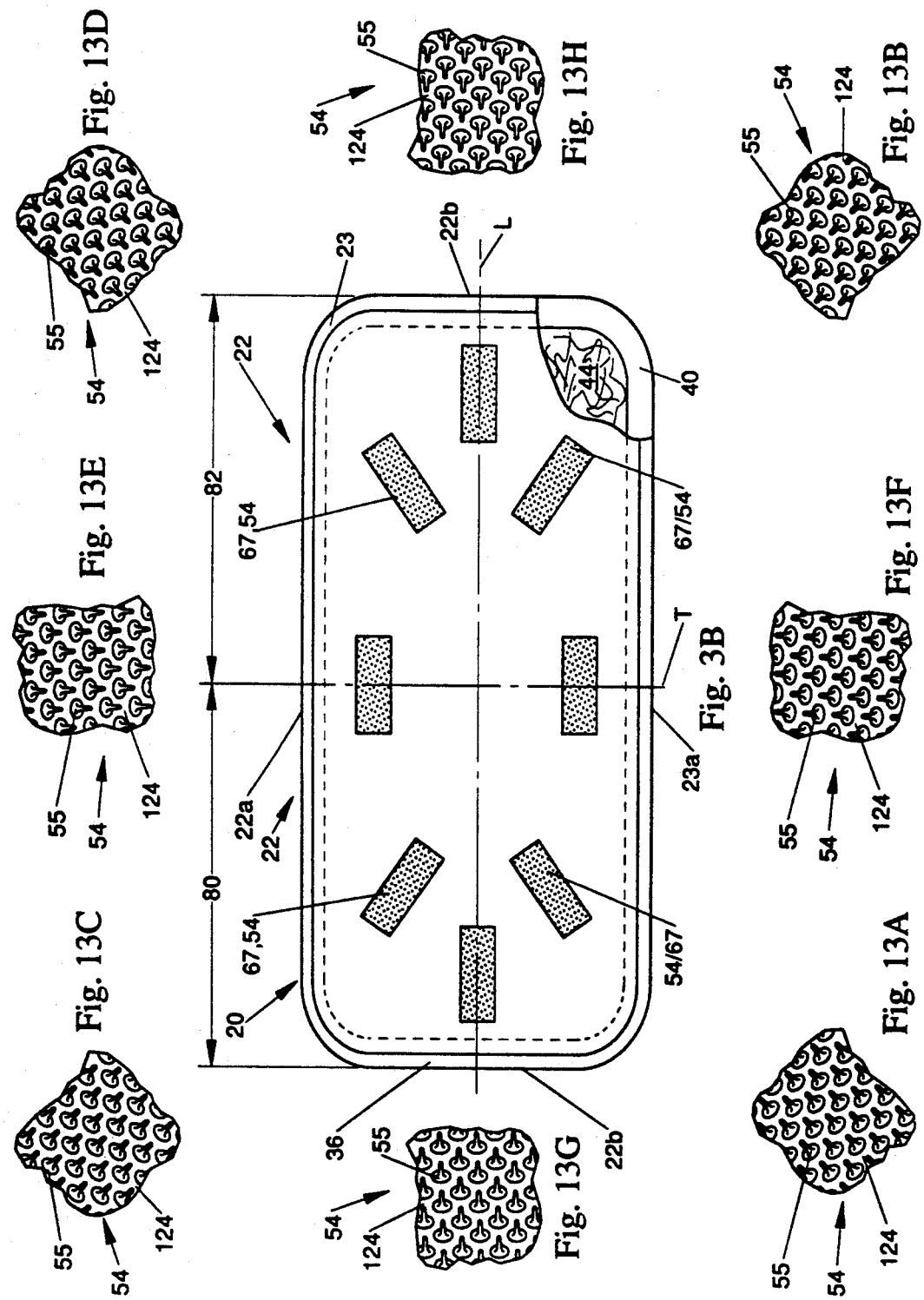

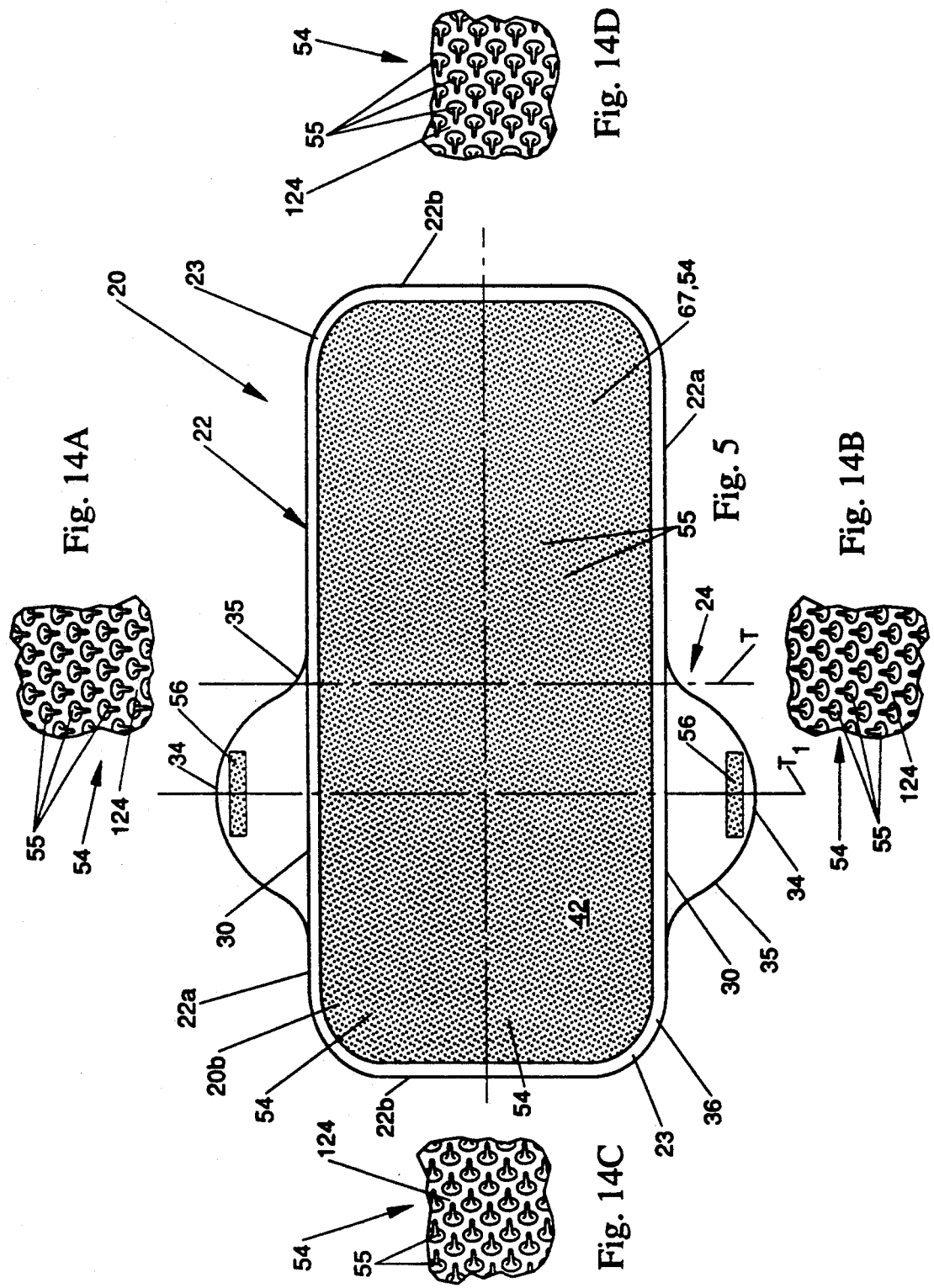

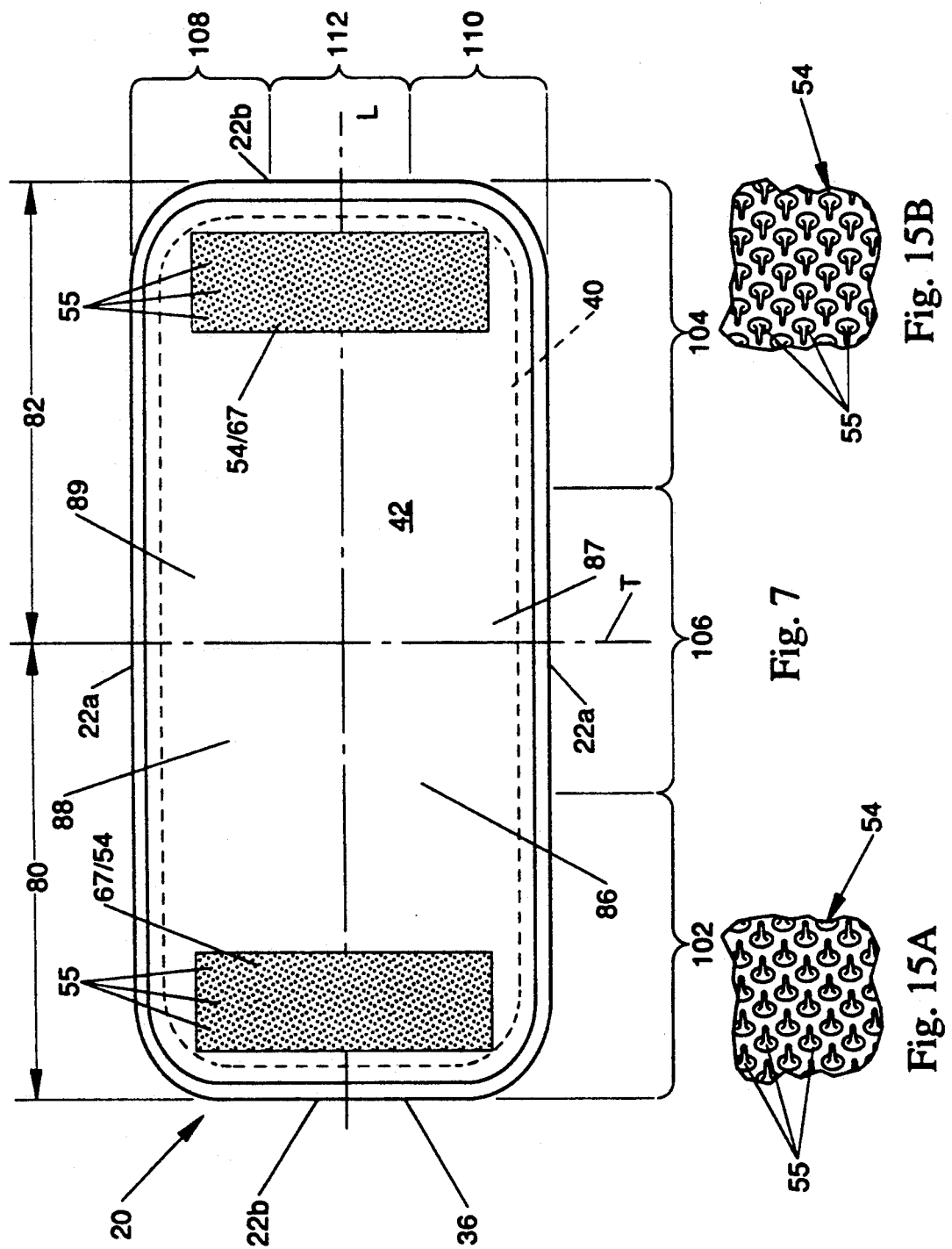

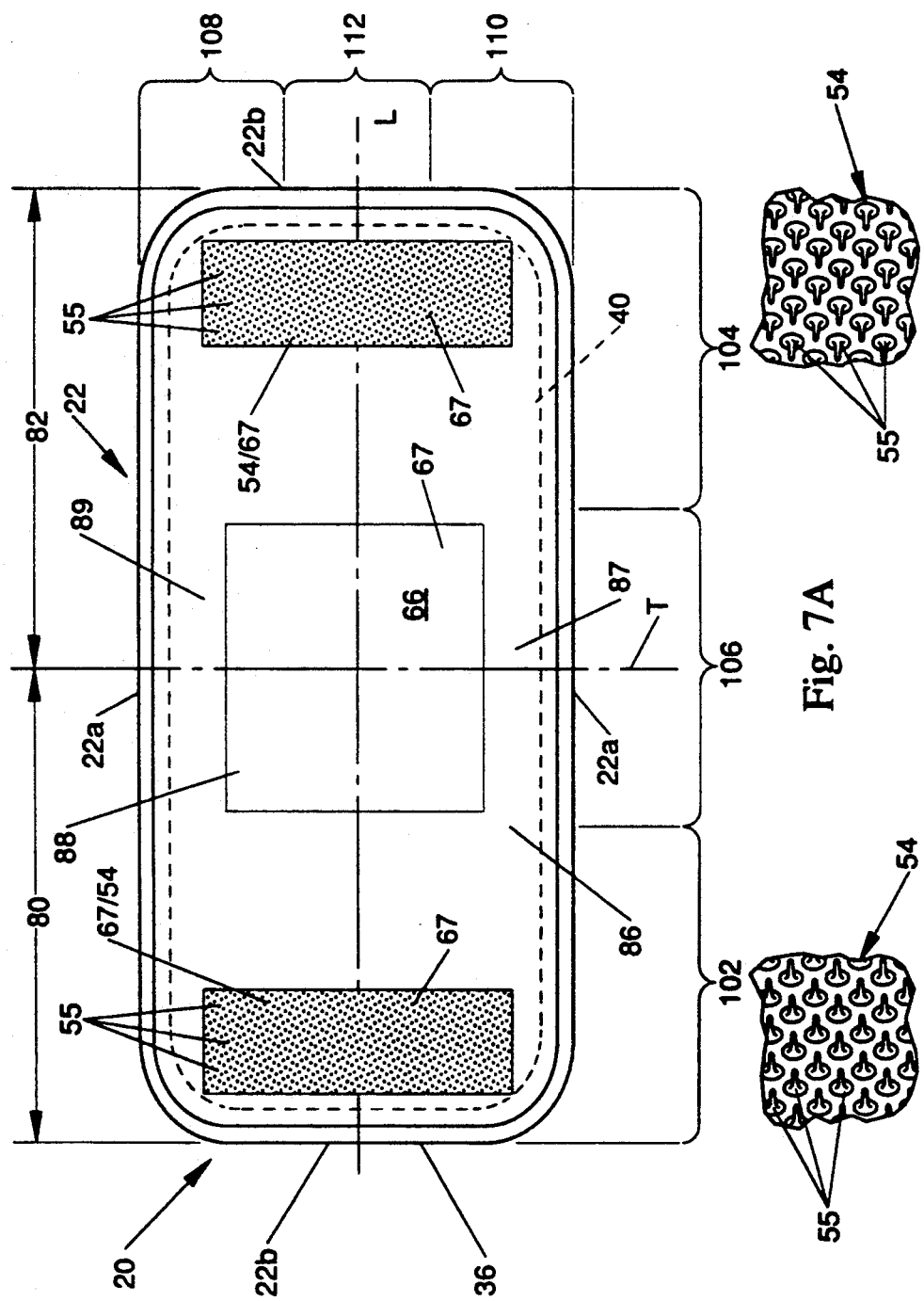

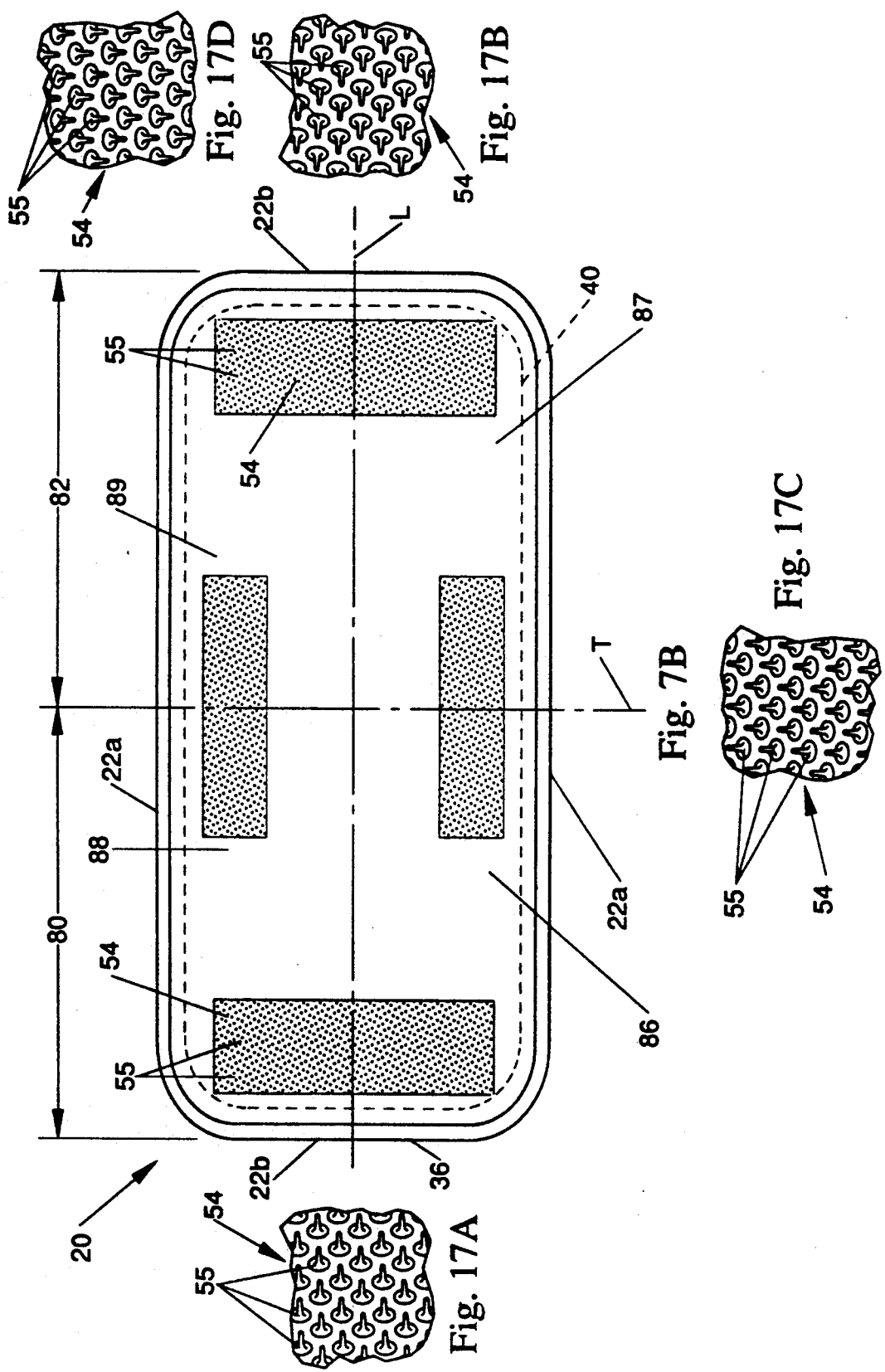

DISPOSABLE ABSORBENT ARTICLE HAVING AN IMPROVED MECHANICAL FASTENING SYSTEM

FIELD OF THE INVENTION

The present invention relates to disposable absorbent articles having mechanical fastening systems, more particularly to an absorbent pad, such as a sanitary napkin or incontinent pad, which is positioned and worn in the crotch portion of the wearer's panties or other undergarment.

BACKGROUND OF THE INVENTION

All manner and variety of absorbent articles configured for the absorption of body fluids such as menses, urine, and feces are, of course, well known. Absorbent articles, particularly sanitary napkins, pantiliners, incontinent pads, and the like are disclosed in the literature and are available in the marketplace.

Generally, absorbent articles will comprise a central absorbent means or central pad which is provided with a means for securing the central pad to the crotch of a wearer's undergarment. Currently available absorbent articles, particularly sanitary napkins and pantiliners, are positioned in an undergarment, such as woman's panties, and secured thereto by pressure-sensitive adhesive. While the use of adhesive is common, there are a number of drawbacks such as comfort, adhesive contamination, residual build-up on panties, the inconvenience of and noise produced by the protective sheets, and the like.

Absorbent articles having wings or flaps are also disclosed in the literature and are available in the marketplace. Generally, the flaps of such absorbent articles extend laterally from a central absorbent means and are intended to be folded around the edges of the wearer's panties in the crotch region. Thus, the flaps are disposed between the edges of the wearer's panties in the crotch region and the wearer's thighs. Commonly, the flaps are provided with an adhesive attachment means, or flap adhesive, for affixing the flaps to the underside of the wearer's panties.

The flaps serve at least two purposes. First, the flaps prevent exudates which otherwise would soil the edges of the wearer's panties from doing such. Second, the flaps help stabilize the napkin from shifting out of place, especially when the flaps are affixed to the underside of the panties.

Sanitary napkins having flaps of various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,271, entitled "Sanitary Napkin", which issued to Clark on Apr. 2, 1957, all of which patents are incorporated herein by reference.

A common problem with disposable absorbent articles such as sanitary napkins, is that the central absorbent means will frequently shift from its original position during wear due to stresses caused by body motion and/or the pressure of the thighs and buttocks. Shifting can also occur when the wearer's pants (or other outer garment) are being pulled up. This is particularly true if the wearer's pants are tight-fitting. If the fastener which holds the central absorbent means to the crotch of the wearer's panties is an adhesive fastener, then this shifting of the absorbent article can result in the central pad adhesive sticking to itself causing "bunching" of the central absorbent means within the panty. Shifting of the central absorbent means may also occur if the adhesive of the adhesive fastener is aged or if there is insufficient adhesive.

In addition to the shifting and bunching of the central absorbent means, a common problem with disposable absorbent articles having flaps or wings, is that the fasteners which hold the flaps to the wearer's panties will frequently "pop" loose from the panty when the panty is being pulled up or when the wearer's pants (or other outer garment) are being pulled up. Again, this is particularly true if the wearer's panty, pants, or other outer garment are tight-fitting. If the fastener which hold the flaps to the wearer's panties is an adhesive fastener, then this popping loose of the fastener can result in the flap adhesive sticking to itself, to the body of the wearer, or to an extraneous surface.

Mechanical fasteners are an alternative to pressure sensitive adhesives. Absorbent articles having mechanical fastener means are disclosed in the art. Although the use of mechanical fasteners avoids some of the drawbacks of the adhesive fasteners such as adhesive contamination, residual build-up on panties, and the inconvenience of and noise produced by the protective sheets, disposable absorbent articles using mechanical fasteners are still subject to the shifting of the central absorbent means and the popping loose of the flap adhesives upon application of the wearer's pants. Disposable absorbent articles using mechanical fasteners generally do not suffer from "bunching" as do disposable absorbent articles using adhesive fasteners. However, disposable absorbent articles using mechanical fasteners will still suffer from misalignment in the crotch of the wearer's panties as a result of shifting of the central absorbent means and will still suffer from the flaps popping loose.

Therefore, there is a need for an absorbent article comprising a mechanical fastener which can hold the flaps securely to the crotch of a wearer's undergarment without popping loose upon application of the wearer's pants or other outer garment. There is also a need for an absorbent article comprising a mechanical fastener which can hold the absorbent article securely in place without unwanted shifting of the central absorbent means upon application of the wearer's pants or other outer garment. There is also a need for an absorbent article comprising a mechanical fastener which can hold the absorbent article securely in place without unwanted shifting of the absorbent article during use.

It is therefore an object of the present invention to provide a disposable absorbent article comprising a mechanical fastener which can maintain the absorbent article securely in the panty of the user without popping loose upon pulling up the wearer's panty, pants, or other outer garment.

It is also an object of the present invention to provide a disposable absorbent article comprising a mechanical fastener which can maintain the absorbent article securely in the panty of the user without unwanted shifting of the absorbent article.

It is also an object of the present invention to provide an absorbent article comprising a mechanical fastener having engaging elements which are arranged such that any shifting of the absorbent article will tend to improve the positioning of the absorbent article in the undergarment.

It is an additional object of the present invention to provide a disposable absorbent article comprising a mechanical fastener which tends to maintain the absorbent article in intimate contact with the body of the wearer.

It is an additional object of the present invention to provide a disposable absorbent article comprising a mechanical fastener which does not need a dedicated receiving surface but which can be secured to the panty material or the materials of the disposable absorbent article itself.

SUMMARY OF THE INVENTION

The present invention relates to an absorbent article for wearing in the crotch region of an undergarment which is comprised of a fibrous material.

The absorbent article has a body-facing side and a garment side. The absorbent article comprises a main body portion having an absorbent assembly capable of absorbing fluids and a principal transverse centerline which divides the main body portion into a first half and a second half. The absorbent article additionally comprises an oriented hook fastening material joined to the garment side of the first half and an oriented hook fastening material joined to the garment side of the second half. The oriented hook fastening materials comprise a plurality of engaging elements joined to a substrate and are generally oriented in a direction having a vector component perpendicular to the principle transverse centerline of the main body portion.

In an alternate embodiment of the present invention, the disposable absorbent article will have side flaps joined to the main body portion and an oriented hook fastening material joined to the side flaps.

In another alternate embodiment of the present invention, the disposable absorbent article will have a combination of a pressure sensitive adhesive and an oriented mechanical fastening system.

BRIEF DESCRIPTION OF THE DRAWINGS

While the specification concludes with claims particularly pointing out and distinctly claiming the invention, it is believed the invention will be better understood from the following description taken in conjunction with the associated drawings in which like elements are described by the same reference numeral or letter and related elements are designated by adding one or more prime symbols:

FIG. 1 is a top plan view of a sanitary napkin embodiment of the present invention with the garment side facing the viewer;

FIG. 1a is a sectional view of the sanitary napkin of FIG. 1 taken along section line a—a;

FIG. 2 is a top plan view of an alternate sanitary napkin embodiment of the present invention with the garment side facing the viewer;

FIG. 3 is a top plan view of an alternate sanitary napkin embodiment of the present invention with the garment side facing the viewer;

FIG. 3a is a top plan view of an alternate sanitary napkin embodiment of the present invention with the garment side facing the viewer;

FIG. 3b is a top plan view of an alternate sanitary napkin embodiment of the present invention with the garment side facing the viewer;

FIG. 5 is a top plan view of an alternate sanitary napkin embodiment of the present invention with the garment side facing the viewer and having flaps joined to the main body portion;

FIG. 7 is a top plan view of an alternate sanitary napkin embodiment of the present invention with the garment side facing the viewer;

FIG. 7a is a top plan view of an alternate sanitary napkin embodiment of the present invention with the garment side facing the viewer; and FIG. 7b is a top plan view of an alternate sanitary napkin embodiment of the present invention with the garment side facing the viewer;

FIG. 8A is an enlarged top plan view of a portion of the garment side of the sanitary napkin of FIG. 1 in the first half;

FIG. 8B is an enlarged top plan view of a portion of the garment side of the sanitary napkin of FIG. 1 in the second half;

FIG. 9A is an enlarged partial sectional view of the sanitary napkin of FIG. 1A in the first half;

FIG. 9B is an enlarged partial sectional view of the sanitary napkin of FIG. 1A in the second half;

FIG. 10A is an enlarged top plan view of a portion of the garment side of the sanitary napkin of FIG. 2 in the first quarter;

FIG. 10B is an enlarged top plan view of a portion of the garment side of the sanitary napkin of FIG. 2 in the second quarter;

FIG. 10C is an enlarged top plan view of a portion of the garment side of the sanitary napkin of FIG. 2 in the third quarter;

FIG. 10D is an enlarged top plan view of a portion of the garment side of the sanitary napkin of FIG. 2 in the fourth quarter;

FIG. 11A is an enlarged top plan view of a portion of the garment side of the sanitary napkin of FIG. 3 in the first quarter;

FIG. 11B is an enlarged top plan view of a portion of the garment side of the sanitary napkin of FIG. 3 in the second quarter;

FIG. 11C is an enlarged top plan view of a portion of the garment side of the sanitary napkin of FIG. 3 in the third quarter;

FIG. 11D is a top plan view of a portion of the garment side of the sanitary napkin of FIG. 3 in the fourth quarter;

FIG. 12A is an enlarged top plan view of a portion of the oriented hook fastening material on the garment side of the sanitary napkin of FIG. 3A in the first quarter;

FIG. 12B is an enlarged top plan view of a portion of the oriented hook fastening material on the garment side of the sanitary napkin of FIG. 3A in the second quarter;

FIG. 12C is an enlarged top plan view of a portion of the oriented hook fastening material on the garment side of the sanitary napkin of FIG. 3A in the third quarter;

FIG. 12D is an enlarged top plan view of a portion of the oriented hook fastening material on the garment side of the sanitary napkin of FIG. 3A in the fourth quarter;

FIG. 12E is an enlarged top plan view of a portion of the oriented hook fastening material on the garment side of the sanitary napkin of FIG. 3A in the transverse center;

FIG. 12F is an enlarged top plan view of a portion of the other oriented hook fastening material on the garment side of the sanitary napkin of FIG. 3A in the transverse center;

FIG. 13A is an enlarged top plan view of a portion of the oriented hook fastening material on the garment side of the sanitary napkin of FIG. 3B in the first quarter;

FIG. 13B is an enlarged top plan view of a portion of the oriented hook fastening material on the garment side of the sanitary napkin of FIG. 3B in the second quarter;

FIG. 13C is an enlarged top plan view of a portion of the oriented hook fastening material on the garment side of the sanitary napkin of FIG. 3B in the third quarter;

FIG. 13D is an enlarged top plan view of a portion of the oriented hook fastening material on the garment side of the sanitary napkin of FIG. 3B in the fourth quarter;

FIG. 13E is an enlarged top plan view of a portion of the oriented hook fastening material on the garment side of the sanitary napkin of FIG. 3B in the transverse center;

FIG. 13F is an enlarged top plan view of a portion of the other oriented hook fastening material on the garment side of the sanitary napkin of FIG. 3B in the transverse center;

FIG. 13G is an enlarged top plan view of a portion of the oriented hook fastening material on the garment side of the sanitary napkin of FIG. 3B at the longitudinal center in the first half;

FIG. 13H is an enlarged top plan view of a portion of the oriented hook fastening material on the garment side of the sanitary napkin of FIG. 3B at the longitudinal center in the second half;

FIG. 14A is an enlarged top plan view of a portion of the oriented hook fastening material on the flap of the sanitary napkin of FIG. 5;

FIG. 14B is an enlarged top plan view of a portion of the oriented hook fastening material on the other flap of the sanitary napkin of FIG. 5;

FIG. 14C is an enlarged top plan view of a portion of the garment side of the sanitary napkin of FIG. 5 in the first half;

FIG. 14D is a top plan view of a portion of the garment side of the sanitary napkin of FIG. 5 in the second half;

FIG. 15A is an enlarged top plan view of a portion of the oriented hook fastening material of the sanitary napkin of FIG. 7 in the first half;

FIG. 15B is an enlarged top plan view of a portion of the oriented hook fastening material of the sanitary napkin of FIG. 7 in the second half;

FIG. 16A is an enlarged top plan view of a portion of the oriented hook fastening material of the sanitary napkin of FIG. 7A in the first half;

FIG. 16B is an enlarged top plan view of a portion of the oriented hook fastening material of the sanitary napkin of FIG. 7A in the second half;

FIG. 17A is an enlarged top plan view of a portion of the oriented hook fastening material of the sanitary napkin of FIG. 7B in the first half;

FIG. 17B is an enlarged top plan view of a portion of the oriented hook fastening material of the sanitary napkin of FIG. 7B in the second half;

FIG. 17C is an enlarged top plan view of a portion of the oriented hook fastening material of the sanitary napkin of FIG. 7B at the longitudinal center; and FIG. 17D is an enlarged plan view of a portion of the other oriented hook fastening material of the sanitary napkin of FIG. 7B at the longitudinal center.

DETAILED DESCRIPTION OF THE INVENTION

1. Introduction

A. The Absorbent Article In General

Figure 4A:
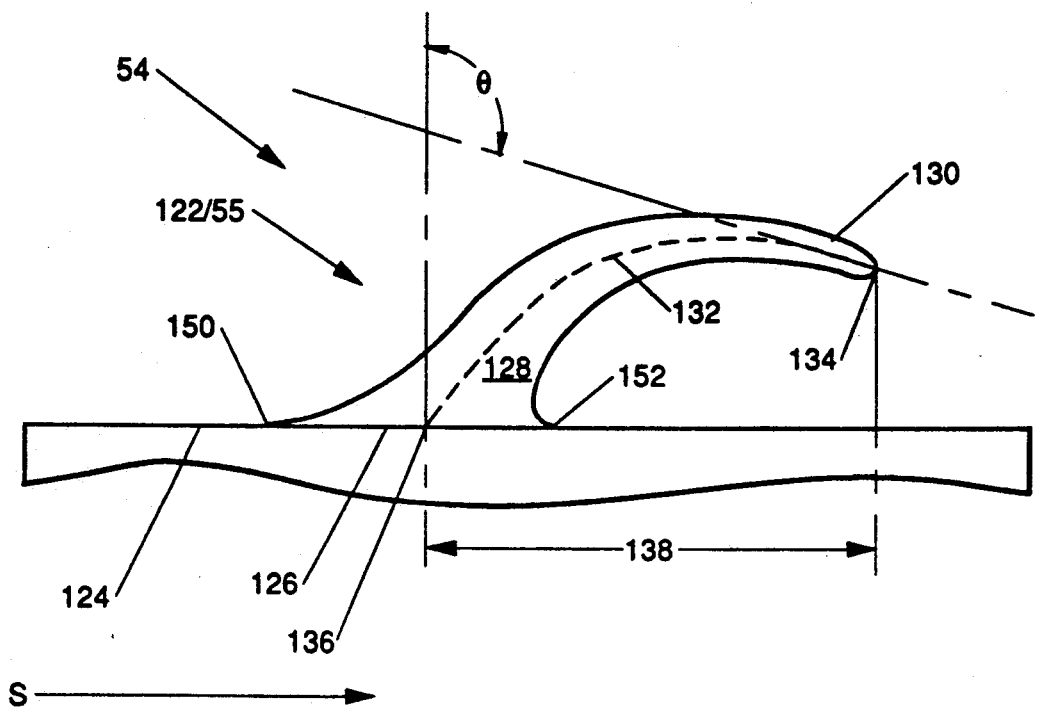
FIG. 4a is a side elevational view of an engaging element of a particularly preferred oriented hook fastening material.

The present invention relates to absorbent articles, such as sanitary napkins. More particularly, the present invention relates to absorbent articles comprising an oriented hook fastening material.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinent pads (and other articles worn in the crotch region of a garment). The term "disposable" refers to articles which are intended to be discarded after a single use and preferably recycled, composted, or otherwise disposed of in an environmentally compatible manner. (That i s, they are not intended to be laundered or otherwise restored or reused as an absorbent article.)

The term "sanitary napkin", as used herein, refers to an article which is typically worn by females adjacent to the pudendal region that is intended to absorb and contain the various exudates which are discharged from the body (e.g., blood, menses, and urine). The present invention, however, is not limited to the particular types or configurations of absorbent articles shown in the drawings.

As used herein, the term "oriented hook fastening material" will refer to a mechanical fastening system having engaging elements that are oriented such that the mechanical fastening system will have little or no shear strength when the mechanical fastening system is moved in a first direction relative to a receiving surface and will have a relatively high shear strength when the mechanical fastening system is moved relative to the receiving surface in the direction opposite the first direction or in a direction having a vector component oriented in a direction opposite the first direction. Having little or no shear strength in a first direction, does not mean that the engaging element or elements of the hook fastening material must break or fail when the hook fastening material is moved in the first direction. It simply means that the engaging elements of the fastening system are arranged, oriented, or configured such that they will not engage the fibers of the receiving surface when the hook fastening material is moved in the first direction. Therefore, the hook fastening material should be able to move in the first direction with relative ease. Having a relatively high shear strength in a direction opposite the first direction, means that the arrangement, orientation, or configuration of the engaging elements of the mechanical fastening system, is such that the engaging elements will engage the fibers of the receiving surface when the hook fastening material is moved in a direction opposite the first direction or is moved in a direction having a vector component oriented in a direction opposite the first direction. Therefore, the mechanical engagement of the engaging elements with the receiving surface will restrict or substantially prevent movement of the hook fastening material in the direction opposite the first direction or in a direction having a vector component oriented in a direction opposite the first direction.

It is not necessary that all of the engaging elements of the hook fastening material be oriented in the same direction. It is only necessary that a sufficient number of engaging elements be oriented to provide the hook fastening material with little or no sheer strength in a first direction and a relatively high sheer strength in a direction opposite the first direction. It will be clear to one skilled in the art that the direction of orientation of a hook fastening material will be generally determined by the direction of orientation of a majority of the engaging elements of that hook fastening material.

As used herein, the term "engaging elements" will refer to the elements of a hook fastening material which are intended to mechanically engage the fibrous elements of a receiving surface such as woven or nonwoven fabrics or loop fastening materials which are well known in the art.

Suitable receiving surfaces for use with the present invention include knitted fabrics, nonwoven materials, reticulated foams, and stitchbonded loop materials, such as Velcro brand loop materials sold by Velcro USA of Manchester, N.H. Particularly preferred receiving surfaces are the woven material of a woman's undergarment and the nonwoven elements of the sanitary napkin such as the topsheet material or flap material.

The terms "oriented hook fastening material" and "hook fastening material" will be used interchangeably herein. It should be understood that the use of the term "hook" should be non-limiting in the sense that the engaging elements may comprise any shapes known in the art so long as they are adapted to engage a loop fastening material or other fibrous material.

A preferred embodiment of an absorbent article of the present invention, sanitary napkin 20, is shown in FIG. 1. As shown in FIG. 1, the sanitary napkin 20 basically comprises an absorbent means represented by central absorbent pad (or "main body portion") 22 and a pad securement member 67 comprising an oriented hook fastening material 54, joined thereto. The main body portion 22 is divided into a first half 80 and a second half 82 by a principle transverse centerline T. An oriented hook fastening material 54 is joined to the first half 80 and second half 82 of the main body portion 22 such that the hook fastening material of the first half 80 is oriented in a direction substantially opposite to the direction of orientation of the hook fastening material of the second half 82. However, both the hook fastening material of the first half 80 and the hook fastening material of the second half 82 are oriented toward the transverse centerline.

In addition to the principal transverse centerline T, the sanitary napkin 20 has a principal longitudinal centerline L which divides the main body portion into four quarters, 86, 87, 88, and 89. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The term "transverse" used herein refers to a line, axis or direction which lies within the plane of the sanitary napkin 20 that is generally perpendicular to the longitudinal direction.

If the sanitary napkin is provided with flaps or wings, then the sanitary napkin will also have a flap transverse centerline $T_1$ which is parallel to the principle transverse centerline T and bisects the flaps or wings of the sanitary napkin 20 as shown in FIG. 5. In some embodiments, the flaps 24 may be positioned slightly forward of the principal transverse centerline T of the sanitary napkin. In such a case, the flap transverse centerline $T_1$ does not coincide with the principal transverse centerline T of the sanitary napkin. The flaps 24, however, are preferably evenly spaced from the principal longitudinal centerline L of the sanitary napkin.

The sanitary napkin 20 is comprised of a topsheet 40, a backsheet 42, and an absorbent core 44. At least a part of the topsheet 40, backsheet 42, and absorbent core 44 comprise the main body portion 22. The hook fastening material 54 is comprised of an array of engaging elements 55 joined to a substrate 124. As used herein, the term "joined" encompasses configurations whereby an element is directly secured to the other element by affixing the element directly to the other element; configurations whereby the element is indirectly secured to the other element by affixing the element to intermediate member(s) which in turn are affixed to the other element; and configurations whereby one element is integral with the other element, i.e., one element is essentially part of the other element. The substrate 124 of the hook fastening material 54 may be comprised of portions of the garment side 20b of the sanitary napkin 20, e.g., the engaging elements are secured directly to the backsheet 42 of the sanitary napkin 20, as shown in FIGS. 1 and 1a. (In alternative embodiments, such as that shown in FIG. 3, the substrate 124 of the hook fastening material 54 may be comprised of a discrete piece (or pieces) of material which is joined to the garment side 20b of the sanitary napkin 20, e.g., the engaging elements are indirectly secured to the backsheet 42 of the sanitary napkin 20.)

2. The Individual Components of the Absorbent Article

The individual components of the sanitary napkin 20 will first be looked at in greater detail.

A. The Topsheet

The topsheet 40 is liquid permeable and when the sanitary napkin 20 is in use, the topsheet 40 is in close proximity to the skin of the user. The topsheet 40 is compliant, soft feeling, and non-irritating to the user's skin. It can be made from any of the materials conventional for this type of use. Nonlimiting examples of suitable materials that can be used as topsheet 40 are woven and nonwoven polyester, polypropylene, nylon, and rayon and formed thermoplastic films, with formed films being preferred.

Suitable formed films are described in U.S. Pat. No. 3,929,135, entitled "Absorptive Structure Having Tapered Capillaries", which issued to Thompson on Dec. 30, 1975, U.S. Pat. No. 4,324,426, entitled "Disposable Absorbent Article Having A Stain-Resistant Topsheet", which issued to Mullane and Smith on Apr. 13, 1982, U.S. Pat. 4,342,314, entitled "Resilient Plastic Web Exhibiting Fiber-Like Properties", which issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which issued to Ahr, Louis, Mullane, and Ouellette on Jul. 31, 1984. Formed films are preferred for topsheet 40 because they are pervious to liquids and yet non-absorbent. Thus, the surface of the formed film which is in contact with the body remains dry and is more comfortable to the wearer.

The sanitary napkin 20 may also be comprised of components that are extensible (i.e., capable of stretching, particularly in the longitudinal direction) when the sanitary napkin is worn. The sanitary napkin 20 may be capable of elongating between about 15% and about 40% of its unstretched length. This extensibility provides better in-use fit, comfort, and decreased staining. In other embodiments, only limited portions of the components of the sanitary napkin 20 are capable of stretching. Such an embodiment (without the oriented hook fastening material of the present invention) is described in greater detail in copending, commonly-assigned U.S. patent application Ser. No. 07/769,891, "Absorbent Article Having Flaps and Zones of Differential Extensibility", filed Oct. 1, 1991, in the name of Bruce Lavash, et al.

A particularly preferred topsheet 40 for use in such an embodiment is one which is made in accordance with U.S. Pat. No. 4,463,045 and ring rolled to provide it with a degree of longitudinal extensibility. Suitable processes for ring rolling or "precorrugating" are described in U.S. Pat. No. 4,107,364 issued to Sisson on Aug. 15, 1978, U.S. Pat. No. 4,834,741 issued to Sabee on May 30, 1989 and in copending, commonly assigned U.S. patent application Ser. No. 07/662,536 entitled "Improved Method And Apparatus For Incrementally Stretching A Zero Strain Stretch Laminate Web To Impart Elasticity Thereto" filed by Gerald M. Weber et al. on Feb. 28, 1991, U.S. patent application Ser. No. 07/662,537 entitled "Improved Method and Apparatus For Incrementally Stretching Zero Strain Stretch Laminate Web In A Non-Uniform Manner To Impart A Varying Degree of Elasticity Thereto" filed by Kenneth B. Buell et al. on Feb. 28, 1991, and U.S. patent application Ser. No. 07/662,543 entitled "Improved Method And Apparatus For Sequentially Stretching Zero Strain Stretch Laminate Web To Impart Elasticity Thereto Without Rupturing The Web" filed by Gerald M. Weber et al . on Feb. 28, 1991. The fold lines in the corrugations of the topsheet should run in the transverse direction so the topsheet is longitudinally extensible.

Such a topsheet is described in greater detail in the following patent applications which were filed on Jun. 23, 1991: U.S. patent application Ser. No. 07/734,404 entitled "Absorbent Articles, Especially Catamenials, Having Improved Fluid Directionality, Comfort and Fit" filed in the names of Thompson, et al.; U.S. patent application Ser. No. 07/734,392 entitled "Fluid Handling Structure for Use in Absorbent Articles" filed in the names of Thompson, et al.; and, U.S. patent application Ser. No. 07/734,405 entitled "Absorbent Core for Use in Catamenial Products" filed in the names of Buenger, et al. These patent applications may be referred to collectively as the "Capillary Channel Fiber" patent applications.

In addition, in preferred embodiments of the present invention, at least a portion of the outer surface 40a of the topsheet 40 is treated with a surfactant. It is preferred that the surfactant be substantially evenly and completely distributed across at least the portion of the outer surface 40a of topsheet 40 that overlays the main body portion 22. This can be accomplished by any of the common techniques well known to those skilled in the art. For example, the surfactant can be applied to topsheet 40 by spraying, by padding, by the use of transfer rolls, or by incorporating the surfactant into the formulation of the topsheet.

Treating the outer surface 40a of the topsheet 40 with a surfactant renders the surface of the topsheet 40 more hydrophilic. This results in liquid penetrating the topsheet 40 faster than it would if the surface were not treated. This diminishes the likelihood that menstrual fluids will flow off topsheet 40 rather than being absorbed by the absorbent core 44. Preferably, any portions of the topsheet 40 that overlay the flaps 24 are not treated with the surfactant. This will minimize any tendencies fluids may have to spread laterally across the flaps and to come in contact with the wearer's thighs and other parts of the wearer's body or garments.

In preferred embodiments, the inner surface 40b of topsheet 40 is secured in contacting relation with the absorbent core 44. This contacting relationship results in liquid penetrating topsheet 40 faster than if the topsheet 40 were not in contact with absorbent core 44. The topsheet 40 can be maintained in contact with absorbent core 44 by applying adhesive to the inner surface 40b of the topsheet 40. Suitable adhesives useful for this purpose are described in U.S. Pat. No. 4,917,697. The adhesives can be applied by the same methods as the surfactant is applied to the outer surface 40a of the topsheet 40.

B. The Absorbent Core

The absorbent core 44 is positioned between the topsheet 40 and the backsheet 42. The absorbent core 44 provides the means for absorbing menstrual fluid. The absorbent core 44 need not have an absorbent capacity much greater than the total amount of menstrual fluid anticipated to be absorbed. The absorbent core 44 is generally compressible, conformable, and non-irritating to the user's skin. It can comprise any material used in the art for such purpose. Examples include comminuted wood pulp which is generally referred to as airfelt, creped cellulose wadding, absorbent foams, absorbent sponges, synthetic staple fibers, polymeric fibers, hydrogel-forming polymer gelling agents, peat moss, or any equivalent material or combinations of materials.

Polymeric gelling agents are those materials which, upon contact with fluids (i.e., liquids) such as water or body fluids, imbibe such fluids and thereby form hydrogels. In this manner, fluids discharged into the absorbent core 44 can be acquired and held by the polymeric gelling agent, thereby providing the articles herein with enhanced absorbent capacity and/or improved fluid retention performance.

The polymeric gelling agent which is employed in the absorbent core 44 will generally comprise particles of a substantially water-insoluble, slightly cross-linked, partially neutralized, hydrogel-forming polymer material. The term "particles", as used herein, can refer to particles in any form, such as in the form of pellets, flakes, or fibers. The characteristics of the absorbent core 44 (including, but not limited to the preferred types of polymer materials used therein, and types of methods which can be used for preparing these polymer particles) are described in greater detail in U.S. Pat. No. 5,009,653 issued to Osborn and the patents incorporated by reference in that patent, the disclosures of which are all incorporated by reference herein.

In one preferred embodiment, the absorbent core 44 is a laminate comprised of a layer of superabsorbent polymer material, such as in the form of particles, disposed between two air-laid tissues, first and second tissue layers (or "upper" and "lower" tissue layers). The first and second tissue layers provide containment of the superabsorbent polymer material, improve lateral wicking of the absorbed exudates throughout the absorbent core 44 and provide a degree of absorbency.

A suitable laminate is the superabsorbent laminate WATER-LOCK L-535 available from the Grain Processing Corporation of Muscatine, Iowa (WATER-LOCK registered TM by Grain Processing Corporation). Such superabsorbent laminates are disclosed in U.S. Pat. No. 4,467,012, entitled "Composition For Absorbent Film And Method Of Preparation", which issued to Pedersen et al. on Aug. 21, 1984, and U.S. Pat. No. 4,260,443, entitled "Laminated Absorbent Process", which issued to Lindsay et al. on Apr. 7, 1981.

The absorbent core 44 may be a laminate, as described above, which is slitted or partially slitted for longitudinal extensibility. This slitted or partially slitted core is described in greater detail in the Capillary Channel Fiber patent applications.

C. The Backsheet

The backsheet 42 is impervious to liquids and, thus, prevents menstrual fluid from soiling the clothing of the user. Any material used in the art for such purpose can be utilized herein. Suitable materials include embossed or nonembossed polyethylene films and laminated tissue. A suitable polyethylene film is manufactured by Monsanto Chemical Corporation and marketed in the trade as Film No. 8020.

In one alternative embodiment of the sanitary napkin 20 (typically in which the topsheet 40 overlays only the main body portion 22 and does not extend out to form the top surface of the flaps), the backsheet 42 may be comprised of two layers. In such a case, the backsheet 42 may comprise a first layer of lofted material disposed on the core-facing side 42a of the backsheet. The purpose of the first layer is to provide a comfortable, non-irritating surface against the body of the wearer. The lofted layer may be comprised of any suitable material, such as a nonwoven material. Preferably, the lofted layer comprises a hydrophobic nonwoven material. The second layer may be disposed on the garment side 42b of the backsheet 42, and may comprise a fluid impervious film. A low density polyethylene material about 0.01 to about 0.05 millimeters in thickness, preferably about 0.02 millimeters in thickness, has been found to work well as this second layer. A polyethylene film, such as is sold by the Ethyl Corporation, Visqueen Division, under model XP-39385 has been found particularly well suited for this second layer. The backsheet 42 may also be made of a soft, cloth-like material which is hydrophobic relative to the topsheet 40. A polyester or polyolefinic fiber backsheet 42 has been found to work well. A particularly preferred soft, cloth-like backsheet 42 material is a laminate of a polyester nonwoven material and a film such as described in U.S. Pat. 4,476,180 issued to Wnuk on Oct. 9, 1984.

A particularly preferred extensible backsheet 42 is an extended adhesive film Formula #198-338 manufactured by the Findley Adhesives Company of Wauwatosa, Wis. which is described in greater detail in the Capillary Channel Fiber patent applications.

3. Assembly of Components into a Sanitary Napkin

A. Assembly of Components

As shown in FIGS. 1 and 1a, the topsheet 40 is secured to backsheet 42 along a first seam, such as seam 36. The seam 36 can be formed by any means commonly used in the art for this purpose such as by gluing, crimping, or heat-sealing. The seam 36 is illustrated in FIG. 1 as extending completely around the periphery of the main body portion 22. This is a preferred embodiment for ease of construction. (Other means of uniting the various elements can be used.)

The main body portion 22 is the portion of the sanitary napkin 20 that contains an absorbent means, such as absorbent core 44. The main body portion 22 has a liquid pervious body contacting surface (represented in FIG. 1a by topsheet 40) and an opposed liquid impervious surface (represented in FIG. 1a by backsheet 42). It is to be understood that the embodiment illustrated is only one possible embodiment, albeit a preferred one. Other possible embodiments include one in which an absorbent core 44 is essentially completely wrapped with topsheet before it is placed on a backsheet. In another alternative embodiment, the absorbent core 44 may be positioned on the backsheet 42 and then the absorbent core 44 and the backsheet 42 may be essentially completely wrapped with the topsheet 40. The main body portion 22 can also comprise an absorbent core which possesses sufficient integrity to stand alone and is liquid pervious on one surface while the other surface has been treated to render it liquid impervious.

The main body portion 22 may be relatively thick or relatively narrow and thin. A thin main body portion may be desired because it is typically comfortable to the user.

B. Construction and Function of the Oriented Hook Fastening Material

1. Hook Fastening Material

The hook fastening material 54 comprises an array of engaging elements 55 joined to a substrate 124 and provides a secure attachment of the sanitary napkin 20 to the crotch of the user's undergarment. The hook fastening material 54 is joined in a predetermined pattern to the garment side 20b of the sanitary napkin 20, usually the backsheet 42. The hook fastening material 54 will be oriented in a direction having a vector component perpendicular to the principle transverse centerline T. Therefore, as shown in FIGS. 1 and 2, the hook fastening material of the first half 80 and the hook fastening material of the second half 82 will be oriented in substantially opposite directions (as shown in FIG. 1) or will be oriented in directions having vector components oriented in substantially opposite directions (as shown in FIG. 2). This configuration of the hook fastening materials provides a secure attachment of the sanitary napkin 20 to the undergarment by having the engaging elements of the first half 80 and the engaging elements of the second half 82 pulling fibers of the undergarment in opposite directions. This configuration of the hook fastening material 54 also results in the main body portion 22 being maintained in close proximity to the body. Such proximity of the main body portion 22 places it precisely where it should be: very near the body at the vaginal opening. The main body portion 22 can then absorb the vast majority of the menstrual fluid (menses) before it has an opportunity to flow along the sides of the main body portion 22. The function of the sanitary napkin will be described in greater detail with relation to the wearer's undergarments.

It will be apparent to one skilled in the art that the direction of orientation of a hook fastening material will be generally determined by the direction of orientation of a majority of the engaging elements of that hook fastening material. The direction of orientation of an individual engaging element generally corresponds with the direction of orientation of the maximum lateral projection 138 of the engaging element.

Referring to FIG. 4a, the maximum lateral projection 138 is that projection from the origin 136 to the outer periphery of the shank 128 or engaging means 130. The origin 136 of the shank 128 is found with the prong 122 in the profile view (as shown in FIG. 4a). The "origin" of the shank 128 is the point which may be thought of as the center of the base 126, and is typically within the footprint of the base 126. The origin 136 is found by viewing the prong 122, from the side view. The "side view" is any direction radially towards the shank 128 and base 126 which is also parallel to the plane of the substrate 124. The lateral distance between the remote edges 150, 152 of the base 126 footprint for the particular side view under consideration is found, and this distance is bisected, yielding the midpoint of the base 126 for such view. When bisecting the footprint of the base 126 for the particular side view under consideration, minor discontinuities (such as fillets or asperities incident to the attachment to substrate 124) are ignored. This point is the origin 136 of the shank 128.

The side view of the prong 122 which maximizes the lateral projection 138 is the profile view of such prong 122. The side elevational view shown in FIG. 4a is one of the profile views of the prong 122. It will be further apparent to one skilled in the art that there is another profile view, generally 180° opposite from the profile view shown (so that the maximum lateral projection 138 is oriented towards the left of the viewer). Either of the two profile views is generally equally well suited to determine the maximum lateral projection 138 of the prong 122 and, therefore, for determining the direction of orientation of the prong 122.

The engaging elements 55 of an oriented hook fastening material 54 will tend to engage fibers of a receiving surface when the hook fastening material is moved relative to the receiving surface in the same direction as the direction of orientation of the hook fastening material, or in a direction having a vector component oriented in the same direction as the direction of orientation of the hook fastening material. The engaging elements engaging the fibers of the receiving surface will restrict or prevent further movement of the hook fastening material 54 in that direction. When the oriented hook fastening material 54 is moved relative to a receiving surface in the direction opposite the direction of the orientation of the hook fastening material 54, or in a direction having a vector component oriented in the direction opposite the direction of the orientation of the hook fastening material 54, the engaging elements 55 will tend to not engage fibers of the receiving surface and movement of the hook fastening material 54 in that direction will tend to be unrestricted. (The direction of orientation for the engaging elements 55 shown in FIGS. 4a, 4b, 4c, and 4d, is represented by the arrow designated S.)

Referring to FIG. 1, the hook fastening material 54 of the first half 80 is oriented in a direction substantially perpendicular to the principal transverse centerline T. The hook fastening material 54 of the second half 82 is also oriented in a direction substantially perpendicular to the principal transverse centerline T. However, the hook fastening material 54 of the second half 82 is oriented in a direction substantially opposite the direction of orientation of the hook fastening material 54 of the first half 80. (The orientation of the engaging elements is shown more clearly in the circular insets of FIGS. 1-3.)

Figure 4B:
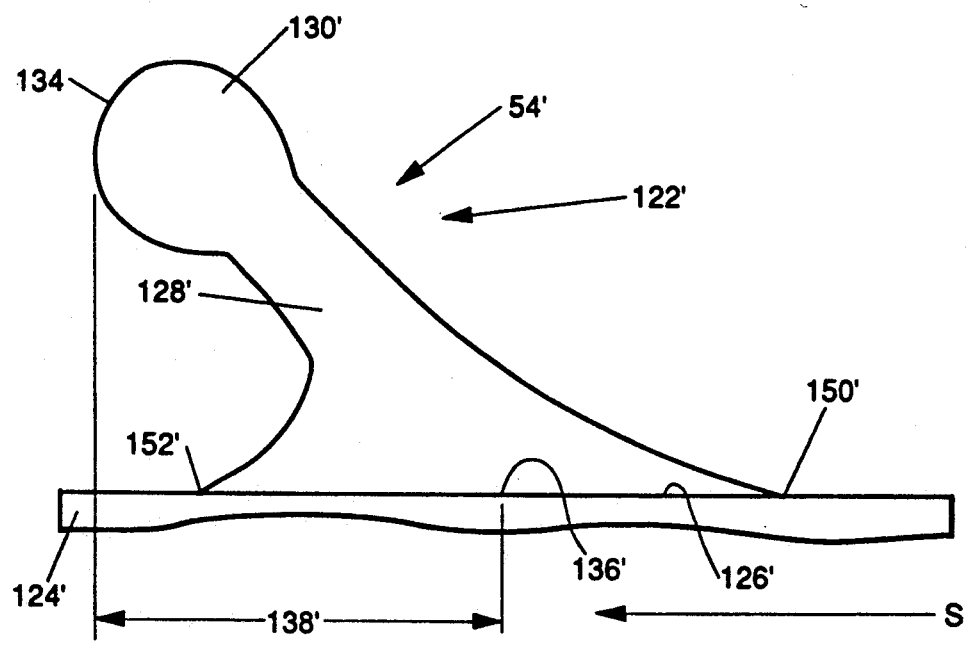
FIG. 4b is a side elevational view of an engaging element of another oriented hook fastening material.
Figure 4C:
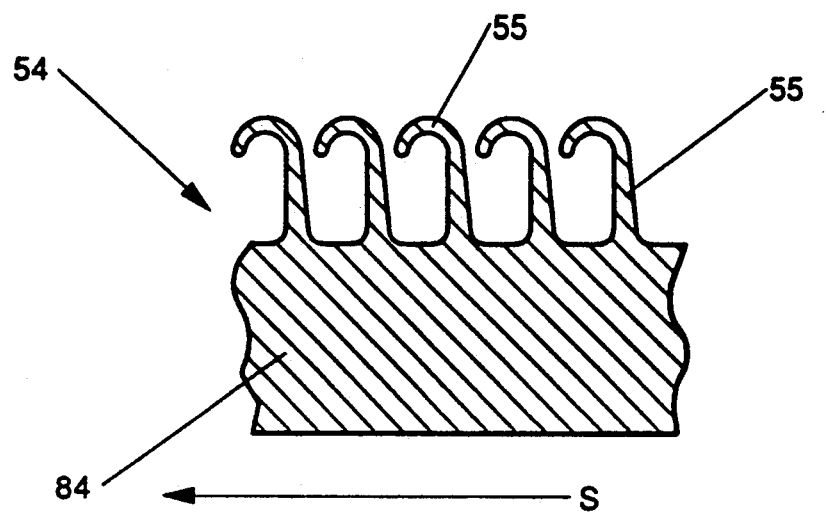
FIG. 4c is a side elevational view of an oriented hook fastening material.
Figure 4D:
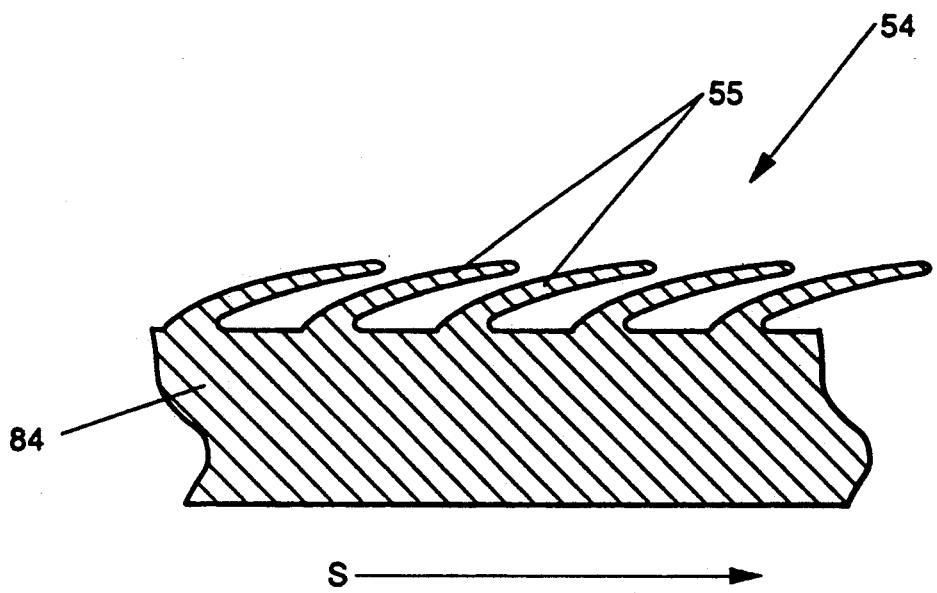
FIG. 4d is a side elevational view of another oriented hook fastenings material.

Although the engaging elements of the hook fastening material are not limited to "hooks", hooks are the preferred engaging element. An especially preferred hook fastening material comprises engaging elements such as the prong 122 shown in FIG. 4a. It should be understood that although a hook fastening material comprising prongs 122 is particularly preferred as the hook fastening material of the present invention, there are other suitable hook fastening materials comprising various suitable engaging elements. Examples of other suitable hook fastening material are shown in FIGS. 4b, 4c, and 4d. However, for clarity and simplicity, the present invention will be described as comprising a hook fastening material 54 such as that depicted in FIG. 4a.

Referring to FIG. 4a, the prong 122 will comprise a base 126, shank 128 and engaging means 130. The base 126 of the prong 122 contacts and adheres to the substrate 124, and supports the proximal end of the shank 128. The shank 128 projects outwardly from the substrate 124 and base 126. The shank 128 terminates at a distal end which is joined to an engaging means 130. The engaging means 130 radially projects laterally (i.e., in a direction having a vector component generally parallel to the plane of the substrate 124 at the principal prong 122 under consideration) from the shank 128 in one or more directions and may resemble a hook-shaped tine. The projection of an engaging means 130 from the shank 128 periphery in a lateral direction allows the engaging means 130 to be secured to a complementary receiving surface (such as the fibrous material of the undergarment 11 shown in FIG. 6). The engaging means 130 is joined to, and preferably contiguous with, the distal end of the prong 122.

Associated with each prong 122 is a longitudinal axis 132. As used herein, the term "longitudinal axis" refers to an imaginary line generally centered at the footprint of the base 126 and laterally and longitudinally projecting through the distal end of the shank 128 to the tip 134 of the engaging means 130. The prong base 126, shank 128 and engaging means 30 are generally concentric with the longitudinal axis 132 if the prong 122 cross section is of a regular shape. If the cross section of the prong 122 is irregularly shaped, the longitudinal axis 132 is disposed at the centroid of any cross section. The "origin" of the longitudinal axis is the same as the origin of the shank, and is found as described hereinbefore.

The engaging means 130 forms an included angle $\theta$ relative to the plane of the substrate 124. As used herein, the term "included angle $\theta$" refers to the angular deviation between the extension of the perpendicular to the plane of the substrate 124 which passes through the origin 136 of base 126 and the projection of the longitudinal axis 132 through the tip 134 of the engaging means 130, as seen when the prong 122 is viewed in profile. The phrase "projection of the longitudinal axis" refers to the imaginary continuation of the longitudinal axis 132 in a straight line through the tip 134 of the engaging means 130 if such axis were continued at the angle present at the tip 134 of the engaging means 130.

It is to be recognized that as the included angle $\theta$ of the engaging means 130 increases, i.e. departs further from the perpendicular to the plane of the substrate 124, it will become increasingly difficult for the engaging means 130 to intercept the strands or fibers of the receiving surface. For any of the embodiments described herein, the engaging means 130 preferably has an included angle $\theta$ of between about 90° to about 160°. More preferably, the included angle $\theta$ is between about 100° to about 150°, and most preferably is between about 110° to about 140°. However, a prong 122 having an included angle $\theta$ greater than about 160° or less than 90° may also be used.

The array of prongs 122 may be produced by any suitable method. Preferably, the prongs 122 are produced by methods which yield free formed prongs. Preferably, the prongs 122 are formed of thermoplastic material, such as hot melt adhesive thermoplastics. Polyester and polyamide hot melt adhesives are particularly well suited for forming the free formed prongs 122 of the preferred hook fastening material 54. The free formed prongs 122 are preferably manufactured using a modified gravure printing process or a screen printing process, by printing the thermoplastic material in its molten state onto a substrate in discrete units, severing the material in a manner that allows stretching of a portion of the thermoplastic material prior to severance, and allowing the stretched molten material to "freeze" resulting in prongs. This preferred hook fastening material and methods and apparatus for making such a hook fastening material are more fully detailed in commonly assigned, co-pending U.S. patent application Ser. No. 07/668,817, "Refastenable Mechanical Fastening System and Process For Manufacture Therefor", filed Mar. 7, 1991, in the name of Dennis A. Thomas; U.S. Pat. No. 5,058,247, issued Oct. 22, 1991 to Dennis A. Thomas and Ted L. Blaney; and U.S. Pat. No. 5,116,563, issued May 26, 1992 to Dennis A. Thomas and David J. K. Goulait.

Methods of orienting the prongs relative to the machine direction, are disclosed in copending, commonly assigned U.S. patent application 07/719,211, "Method for Manufacturing a Refastenable Mechanical Fastening System Having Azimuthally Angled Prongs and Fastening System Produced Therefrom", filed Jun. 21, 1991 in the name of Dennis A. Thomas and David J. K. Goulait, and allowed U.S. patent application 07/632,283, "Process of Manufacturing A Refastenable Mechanical Fastening System", filed Dec. 21, 1990 in the name of Dennis A. Thomas, David J. K. Goulait, and Robert G. Cox, Jr., which patents and patent applications are incorporated herein by reference.

Because the hook fastening material 54 is intended to mechanically engage the fibrous material of the user's undergarment so as to provide a secure attachment of the sanitary napkin 20 to the crotch of the user's undergarment, the prongs 122 are preferably small and the array of prongs is preferably dense, so that the hook fastening material 54 will not irritate the skin of the wearer and will be able to engage the fibers of the wearer's undergarment. A method for making such a dense array of small prongs is disclosed in copending, commonly assigned U.S. patent application 07/718,727, "Screen Printing Method For Manufacturing a Refastenable Mechanical Fastening System and Fastening System produced Therefrom", filed Jun. 21, 1991 in the name of Dennis A. Thomas and David J. K. Goulait, which patent application is incorporated herein by reference.

A fastening system having a dense array of small prongs is preferred because such a fastening system is generally capable of engaging the fibers of the nonwoven materials of the sanitary napkin or the fibers of the wearer's undergarment and does not require a dedicated receiving surface. As used herein, the term "dedicated receiving surface" will refer to any element joined to the sanitary napkin 20 or the undergarment of the wearer, which element has the primary function of acting as the complementary receiving surface for the oriented hook fastening material 54. As used herein, the term "non-dedicated hook fastening material" will refer to a hook fastening material which is capable of engaging the fibers of the nonwoven materials of the sanitary napkin (such as topsheet materials) or the fibers of the wearer's undergarment (such as woven materials) and does not require a dedicated receiving surface. When a non-dedicated hook fastening material 54 is said to be "capable" of engaging the fibers of the nonwoven materials of the sanitary napkin or the fibers of the wearer's undergarment, this means that the materials of the sanitary napkin or undergarment may be used as a receiving surface for the non-dedicated hook fastening material. However, the non-dedicated hook fastening material is typically not limited to use with such receiving surfaces (e.g., materials of the sanitary napkin and materials of the wearer's undergarment) and dedicated receiving surfaces may also be used.

A particularly "skin-friendly" mechanical fastening system and methods of producing such a fastening system are disclosed in commonly assigned, copending, U.S. patent application 07/ "Non-Abrasive Mechanical Fastening System and Process of Manufacture Therefor", which patent application is being filed concurrently herewith in the names of David J. K. Goulait and Dennis A. Thomas, and which is incorporated herein by reference.

The hook fastening material 54 of FIG. 4a may be formed on a substrate 24 discrete from the sanitary napkin 20 and then cut and applied to the sanitary napkin 20. However, the hook fastening material shown in FIG. 4a is particularly preferred because the prongs 122 can be formed directly on the backsheet 42 of the sanitary napkin as the sanitary napkin is being made, and the orientation of the hook fastening material can be controlled by azimuthally angling the individual prongs 122 according to the methods of the above-referenced patents and patent applications.

Another example of a suitable hook fastening material 54' which also can be formed directly on the sanitary napkin, is shown in FIG. 4b. The hook fastening system 54' of FIG. 4b comprises a prong 122 comprising a base 126', shank 128' and a generally semispherically (mushroom) shaped engaging means 130'. The term "semispherical" means a generally round shape, protruding in multiple directions and is inclusive of hemispheres and spheres, but not limited to regular shapes. This geometry, particularly the generally spherically shaped engaging means 130' structure, provides the advantage that less disturbance to the strands of the receiving surface typically occurs when the engaging means 30' is removed from the receiving surface. This causes less visible damage to the receiving surface, allowing it to be reused a greater number of times.

One method for making the hook fastening system 54' of FIG. 4b, is by forming the prongs 122 of FIG. 4a according to the methods of the above-referenced patents and patent applications, and heating the engaging means 130 and distal end of the prong to at least the melting point. This is accomplished by bringing the engaging means 130 and distal ends of the prongs 122 to a heat source longitudinally directed toward the plane of the substrate so that the base 126' and the proximal end of the shank 128' are not heated to at least the melting point. A suitable method is to bring the highest elevation of the prong to within about 3.3 millimeters to about 10.1 millimeters (0.1 to 0.4 inches) of a heat source, such as a hot wire heated to about 440° C.

Methods of forming the prong 122' of FIG. 4b are more fully described in the aforementioned commonly assigned, co-pending U.S. patent application Ser. No. 07/668,817 "Refastenable Mechanical Fastening System and Process For Manufacture Therefor", filed Mar. 7, 1991, in the name of Dennis A. Thomas and U.S. Pat. No. 5,116,563, issued May 26, 1992 to Dennis A. Thomas and David J. K. Goulait, which patents and patent applications are incorporated herein by reference.

Additional examples of suitable oriented hook fastening materials 54, are shown in FIGS. 4c and 4d. The hook fastening materials 54 shown in FIGS. 4c and 4d, comprise engaging elements 55 that are integral with the base materials 84. Methods of producing such fastening materials are disclosed in U.S. Pat. No. 3,557,407, "Apparatus For Surface Forming Sheet Material", issued Jan. 26, 1971.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

2. Function of the Sanitary Napkin

The function of the sanitary napkin of the present invention will now be described in greater detail with relation to the wearer's undergarments.

Figure 6:
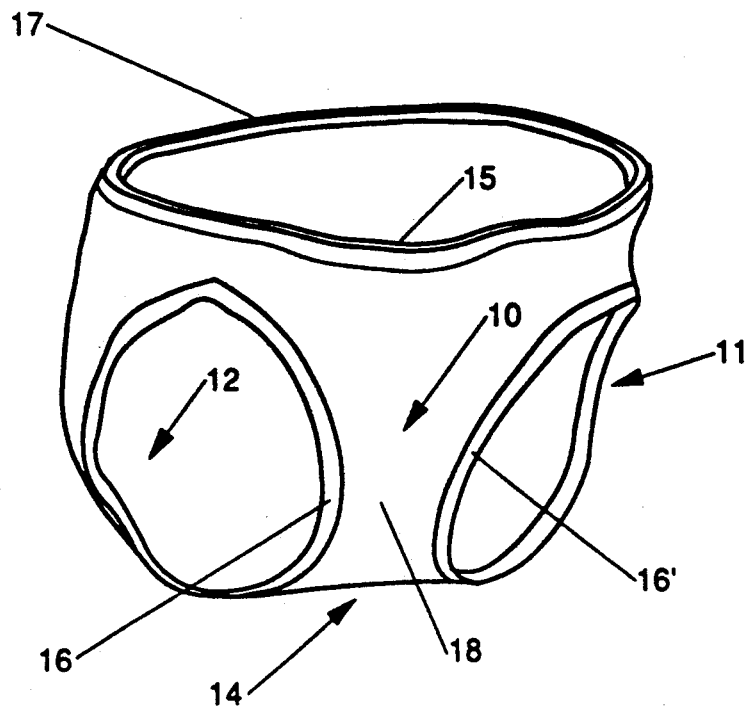
FIG. 6 is a perspective view of the crotch portion of a women's panties.

The hook fastening material of the sanitary napkin 20 provides a secure attachment to an undergarment by creating shear forces on the undergarment that are oriented on substantially opposite directions. FIG. 6 is a depiction of an undergarment 11 of the type commonly worn by many women and well known as a panty. A panty 11 comprises a front section 10, a back section 12, and a crotch portion 14 which joins the front and back sections. The front section 10 extends from the crotch portion 14 to the front waistband 15. The back section 12 extends from the crotch portion 14 to the back waistband 17. The crotch portion 14 comprises two side edges 16, 16' and center crotch portion 18.

Figure 6A:
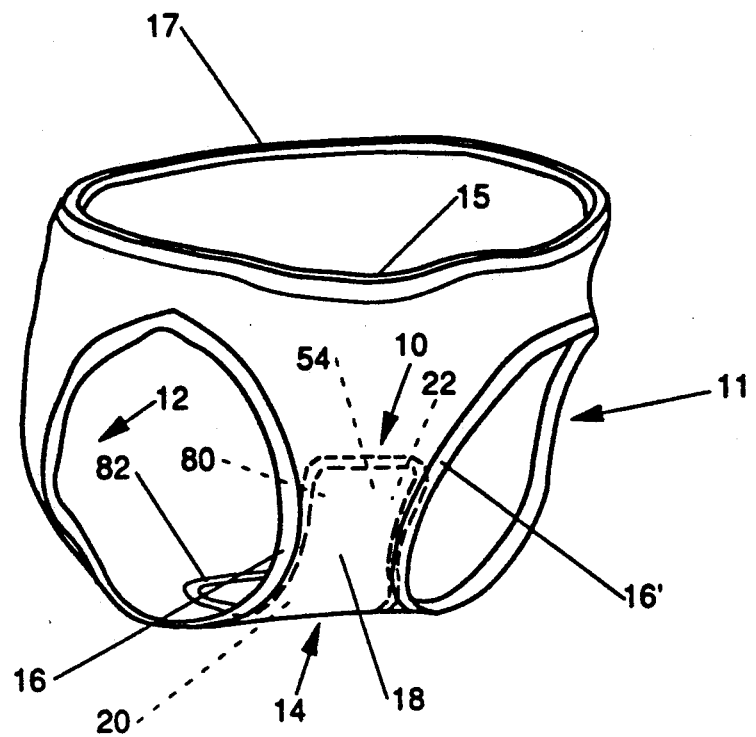
FIG. 6a is the same perspective view of the women's panties shown in FIG. 6 with the sanitary napkin embodiment of the present invention being placed therein for use.

The sanitary napkin 20 of the present invention is utilized by placing the sanitary napkin 20 in a panty 11 as shown in FIG. 6a. The center of main body portion 22 is placed in crotch portion 14 of the panty with the first half 80 of the main body portion 22 extending towards the front section 10 of the panty 11 and the second half 82 of the main body portion 22 extending towards the back section 12 of the panty 11. The oriented hook fastening materials 54 are placed in contact with the inner surface of the crotch portion 14 of the panty 11 such that the engaging elements 55 of the first half 80 mechanically engage the fibers of the front section 10 and the engaging elements 55 of the second half 82 mechanically engage the fibers of the back section 12.

As a result of the engaging elements 55 of the hook fastening material 54 of the first half 80 mechanically engaging the fibers of the front section 10 of panty 11, the first half 80 of the sanitary napkin 20 is restricted or substantially prevented from moving toward the crotch portion 14 of the panty 11. However, the first half 80 of the sanitary napkin 20 is able to move in a direction away from the crotch portion, i.e., toward the front waistband 15 of the panty 11, without mechanically engaging the fibers of the front section 10 of panty 11. Therefore, the first half 80 of the sanitary napkin 20 is able to move toward the front waistband 15 of the panty 11 with relative ease. Accordingly, any movement of the first half 80 of the sanitary napkin 20 will tend to be movement away from the crotch portion 14 of the panty 11, i.e., in the direction of the front waistband 15 of the panty 11.

Likewise, as a result of the engaging elements 55 of the hook fastening material 54 of the second half 82 mechanically engaging the fibers of the back section 12 of panty 11, the second half 82 of the sanitary napkin 20 is restricted or substantially prevented from moving toward the crotch portion 14 of the panty 11. However, the second half 82 of the sanitary napkin 20 is able to move toward the back waistband 17 of the panty 11 without mechanically engaging the fibers of the back section 12 of panty 11. Therefore, the second half 82 of the sanitary napkin 20 is able to move toward the back waistband 17 of the panty 11 with relative ease. Accordingly, any movement of the second half 82 of the sanitary napkin 20 will tend to be movement away from the crotch portion 14 of the panty 11, i.e., in the direction of the back waistband 17 of the panty 11.

This arrangement of the hook fastening materials 54 creates shear forces between the first half 80 of the sanitary napkin 20 and the front section 10 and between the second half 82 of the sanitary napkin 20 and the back section 12. The shear forces of the first half 80 and the second half 82 provide a secure attachment of the sanitary napkin 20 to the panty 11 by having the forces of the first half 80 and the second half 82 opposed to each other.

An additional benefit obtained by this arrangement, is that any movement of the sanitary napkin 20 relative to the panty 11 will tend to be movement of the first half 80 and movement of the second half 82 toward the front waistband 15 and rear waistband, respectively. Therefore, movement of the sanitary napkin relative to the panty 11 tends to draw the sanitary napkin 20 closer to the body of the wearer. This is especially true in embodiments having the transverse center 106 of the sanitary napkin 20 substantially free of any securement member, i.e., hook fastening material, pressure sensitive adhesive, and the like, because the transverse center 106 of the sanitary napkin 20 is then able to decouple from the panty central crotch portion 18 and move closer to the vaginal opening. Such embodiments are shown in FIGS. 3 and 7 and discussed in greater detail hereinbelow.

C. Alternate Embodiments of the Sanitary Napkin of the Present Invention

In an alternate sanitary napkin embodiment embodiment of the present invention shown in FIG. 2, the main body portion 22 is further divided by the longitudinal centerline L into quarters, 86, 87, 88, and 89. Each quarter (86–89) of the main body portion 22 comprises a pad securement member 67 comprising an oriented hook fastening material 54. The hook fastening material 54 of each quarter (86–89) of the main body portion 22 comprises engaging elements 55 oriented in a direction having a vector component perpendicular to the principal transverse centerline T and a vector component perpendicular to the longitudinal centerline L. Such an arrangement results in the shear forces of the hook fastening material 54 being oriented generally toward the point where the longitudinal centerline L and the transverse centerline T intersect.

In another alternate sanitary napkin embodiment of the present invention shown in FIG. 3, the hook fastening material 54 of each quarter (86–89) of the main body portion 22 comprises engaging elements 55 oriented in a direction having a vector component perpendicular to the principal transverse centerline T and a vector component perpendicular to the longitudinal centerline L. However, rather than the entire garment side of each quarter (86–89) being covered with an oriented hook fastening material (as in the embodiment of FIG. 2), only a portion of each quarter (86–89) comprises an oriented hook fastening material. This arrangement leaves the transverse center 106 and the longitudinal center 112 of the sanitary napkin 20 substantially free of any fastening material and will therefore allow the transverse center 106 and the longitudinal center 112 of the sanitary napkin 20 to detach or decouple from the undergarment and may improve the contact of the sanitary napkin 20 with the vaginal opening.

As can be seen in FIGS. 3, 3a, and 3b, the transverse center 106 of the sanitary napkin 20 is that portion of the main body portion 22 which extends transversely from one longitudinal side 22a to the other longitudinal side 22a and extends longitudinally from about the first transverse end 102 to about the other transverse end 104. The first transverse end 102 of the main body portion 22 is that portion of the main body portion 22 which extends transversely from one longitudinal side 22a to the other longitudinal side 22a and extends longitudinally from one transverse side 22b to about the transverse center 106. The second transverse end 104 of the main body portion 22 is that portion of the main body portion 22 which extends transversely from one longitudinal side 22a to the other longitudinal side 22a and extends longitudinally from the other transverse side 22b to about the transverse center 106.

As can be seen in FIGS. 3, 3a, and 3b, the longitudinal center 112 of the main body portion 22 is that portion of the main body portion 22 which extends longitudinally from one transverse side 22b to the other transverse side 22b and extends transversely from about the first longitudinal end 108 to about the second longitudinal end 110. The first longitudinal end 108 of the main body portion 22 is that portion of the main body portion 22 which extends longitudinally from one transverse side 22b to the other transverse side 22b and extends transversely from one longitudinal side 22a to about the longitudinal center 112. The second longitudinal end 110 of the main body portion 22 is that portion of the main body portion 22 which extends longitudinally from one transverse side 22b to the other transverse side 22b and extends transversely from the other longitudinal side 22a to about the longitudinal center 112.

Another alternate sanitary napkin embodiment of the present invention is shown in FIG. 3a. The sanitary napkin of FIG. 3a is substantially the same as that shown in FIG. 3. However, the pad securement member 67 of the sanitary napkin 20 of FIG. 3a comprises two additional patches of an oriented hook fastening material 54. One patch of oriented hook fastening material 54 is positioned at about the transverse center 106 on one side of the principle longitudinal centerline L and is oriented in a direction having a vector component perpendicular to the longitudinal centerline L. The other patch of oriented hook fastening material 54 is positioned at about the transverse center 106 on the other side of the principle longitudinal centerline L and is also oriented in a direction having a vector component perpendicular to the longitudinal centerline L.

Another alternate sanitary napkin embodiment of the present invention is shown in FIG. 3b. The sanitary napkin of FIG. 3b is substantially the same as that shown in FIG. 3a. However, the pad securement member 67 of the sanitary napkin of FIG. 3b comprises two additional patches of an oriented hook fastening material 54. One patch of oriented hook fastening material 54 is positioned at about the longitudinal center 112 on one side of the principle transverse centerline T and is oriented in a direction having a vector component perpendicular to the transverse centerline T. The other patch of oriented hook fastening material 54 is positioned at about the longitudinal center 112 on the other side of the principle transverse centerline T and is also oriented in a direction having a vector component perpendicular to the principle transverse centerline T.

Another alternate sanitary napkin embodiment of the present invention having a transverse center 106 that may detached or decoupled from the undergarment, is shown in FIG. 7. The sanitary napkin 20 of FIG. 7 comprises a pad securement member 67 comprising an oriented hook fastening material 54 positioned at about the first transverse end 102 and another oriented hook fastening material 54 positioned at about the second transverse end 104. Each of the hook fastening materials 54 are oriented in a direction having a vector component perpendicular to the transverse centerline T, and the transverse center 106 is substantially free from any type of fastening member.

Another alternate sanitary napkin embodiment of the present invention is shown in FIG. 7a. The sanitary napkin embodiment of FIG. 7a is substantially the same as that shown in FIG. 7, however, the pad securement member 67 of the sanitary napkin 20 of FIG. 7a additionally comprises a pressure sensitive adhesive 66 positioned in the transverse center 106 of the main body portion 22. The pressure sensitive adhesive 66 would secure the transverse center 106 of the sanitary napkin to the crotch of the panty. Even if the pressure sensitive adhesive 66 shifts during application of the wearer's pants, the oriented hook fastening material 54 would tend to maintain proper positioning of the main body portion 22 in the panty and prevent "bunching" of the main body portion 22.

Another alternative sanitary napkin embodiment is shown in FIG. 7b. The sanitary napkin embodiment of FIG. 7b is substantially the same as that shown in FIG. 7, however, the pad securement member 67 of the sanitary napkin of FIG. 7b comprises two additional patches of an oriented hook fastening material 54. One patch of oriented hook fastening material 54 is positioned at about the transverse center 106 of the sanitary napkin 20 on one side of the principle longitudinal centerline L and is oriented in a direction having a vector component perpendicular to the longitudinal centerline L. The other patch of oriented hook fastening material 54 is positioned at about the transverse center 106 of the sanitary napkin 20 on the other side of the principle longitudinal centerline L and is also oriented in a direction having a vector component perpendicular to the longitudinal centerline L.

An embodiment wherein essentially the entire perimeter of the main body portion comprises a hook fastening material which is oriented in a direction having a vector component perpendicular to the transverse centerline or perpendicular to the longitudinal centerline, is also contemplated. As used herein, the term "perimeter of the main body portion" shall refer to that portion of the main body portion 22 which is substantially adjacent the longitudinal edges 22a and the transverse edges 22b of the main body portion 22. In such an embodiment a portion of the transverse center 106 and a portion of the longitudinal center 112 of the main body portion 22 will be substantially free of any fastening material and will therefore allow that portion of the main body portion 22 to detach or decouple from the undergarment and may improve the contact of the sanitary napkin 20 with the vaginal opening. Alternatively, that portion of the main body portion 22 which is substantially free of any oriented hook fastening material may be provided with an adhesive fastener.

In another alternate embodiment of the present invention, such as that shown in FIG. 5, the sanitary napkin may also comprise wings, or flaps. Generally, flaps extend laterally from the main body portion 22 and are intended to be folded around the edges 16, 16' of the wearer's panty 11 in the crotch region 14. Thus, the flaps are disposed between the edges of the wearer's panties in the crotch region and the wearer's thighs.

The general construction of flaps 24 suitable for use in the present invention (without the oriented hook fastening material 54 of the present invention) is described in greater detail in the patents incorporated by reference herein, such as U.S. Pat. No. 4,917,697 issued to Osborn; U.S. patent application Ser. No. 07/769,891, "Absorbent Article Having Flaps and Zones of Differential Extensibility", filed Oct. 1, 1991 in the name of Bruce Lavash, et al.; and U.S. patent application Ser. No. 07/832,246, "Absorbent Article Having Inwardly-Folded Pleated Flaps", filed Feb. 7, 1992 in the name of Kaoru Niihara and Thomas W. Osborn, III.

The overall size of the flaps 24 can be readily selected by those skilled in the art. Preferably, the flaps 24 are sized so that the sanitary napkin 20 is from about 10 to about 23 centimeters wide between the distal edges 34 of the flaps at their greatest separation. Preferably each flap 24 is from about 5 to at least about 19 centimeters long in the direction parallel to the principal longitudinal centerline L of the sanitary napkin. However, the flaps 24 may be as small as 0.5 centimeters long in the direction parallel to the principle longitudinal centerline L.

The shape of the flaps 24 can be selected by those skilled in the art. Preferably, not only are the flaps 24 mirror images of each other, the two halves of each flap 26 and 28 are also symmetrical about the flap transverse centerline $T_1$. (It should be understood that the shape and orientation of the flaps described herein are those of a preferred embodiment. They are not mandatory design features.)

Preferably, as in the sanitary napkin 20 illustrated in FIG. 5, the flaps 24 are positioned slightly forward of the principal transverse centerline T of the sanitary napkin. (In such a case, the flap transverse centerline $T_1$ does not coincide with the principal transverse centerline T of the sanitary napkin 20.) The flaps 24, however, are preferably evenly spaced from the principal longitudinal centerline L of the sanitary napkin.

In a preferred embodiment, the flaps 24 are joined with the main body portion 22 along lines of juncture 30. The lines of juncture can be concave, straight, (or, but preferably not, convex) relative to the principal longitudinal centerline L. The lines of juncture 30 may comprise those lines or areas where separate flap elements are joined to the main body portion 24. Alternatively, when the flaps 24 are integral with the main body portion 22, the lines of juncture 30 may represent lines of demarcation between the main body portion 22 and the flaps 24 (although it is not necessary that there be a precise line of demarcation).

The flaps 24 can be joined with the main body portion 22 in a number of different manners. Many of the different ways a component (such as the flaps 24) can be "joined to" or "associated with", etc. another component, are set forth in the definitions of these terms contained in U.S. Pat. No. 5,007,906 entitled "Decoupled Sanitary Napkin" which issued to Osborn, et al. on Apr. 16, 1991. When the flaps comprise separate elements, they can be joined to the main body portion 22 by any techniques known to those skilled in the art. Such techniques include, but are not limited to adhesives, heat and/or pressure, ultrasonics, etc.

It is not necessary that the flaps 24 extend from (or be joined along) the longitudinal edges 22a of the main body portion 22. The flaps 24 can joined inward (or "inboard") from the longitudinal edges 22a toward the longitudinal centerline L such as is shown in U.S. Pat. No. 4,900,320 issued to McCoy on Feb. 13, 1990. The flaps 24 can, thus, each be joined to the main body portion 22 along the principal longitudinal centerline L, or along the longitudinal edges 22a of the main body portion 22, or at any place between the principal longitudinal centerline L and the longitudinal edges 22a of the main body portion 22. The flaps 24 will, of course, generally be on opposite sides of the principal longitudinal centerline L.

Referring to FIG. 5, the outer surface of the flap 24, adjacent the distal edge 34 of the flap, preferably comprises a flap securement member such as a pressure sensitive adhesive, a mechanical fastener, or the like. The flap securement member 56 is used to assist in maintaining the flap 24 in position after it is wrapped around the edge of the crotch portion of the panty as described below. The flaps 24 can be maintained in position by attaching the flaps 24 to the undergarment, or to the opposing flap. Suitable adhesive fasteners are described in greater detail in U.S. Pat. No. 4,917,697.

If the flap securement member 56 comprises an adhesive, the adhesive is preferably protected by a release material to protect the adhesive from dirt, to prevent the adhesive from drying out, and keep the adhesive from sticking to extraneous surfaces prior to use. Suitable release liners are described in U.S. Pat. No. 4,917,697. The sanitary napkin 20 may comprise a unitary release member which is joined to the sanitary napkin and eliminates the need for separate pieces of release material. Unitary release members are discussed in greater detail in U.S. patent application 07/906,593, "Absorbent Article Having A Unitary Release Material", filed Jun. 30, 1992 in the name of Bruce W. Lavash et al.

The flap securement member 56 is not limited to adhesive attachment means. Any type of fastener used in the art can be used for such purpose. For example, the flap 24 of sanitary napkin 20, could be secured to the wearer's undergarment by the fastener described in U.S. Pat. No. 4,946,527 entitled "Pressure-Sensitive Adhesive Fastener and Method of Making the Same" issued to Battrell on Aug. 7, 1990. However, embodiments wherein the flap securement member comprises both a hook fastening material and an adhesive are also contemplated.

The flap securement members 56 of the sanitary napkin 20 preferably comprise an oriented hook fastening material 54 such as the hook fastening materials described herein. In a preferred embodiment the flap securement member 56 will comprise an oriented hook fastening material which is oriented in a direction perpendicular to the principle longitudinal centerline L. Such flaps 24 can be used on any of the sanitary napkin embodiments described herein. Additionally, flaps 24 with the oriented hook fastening material 54 may also be used on sanitary napkins having a pad securement member 67 which is comprised of a pressure sensitive adhesive.

Thus, the present invention provides a sanitary napkin having an oriented hook fastening material which improves body contact with the sanitary napkin and, thereby, improves the effectiveness of the sanitary napkin.

While particular embodiments of the present invention have been illustrated and described, it would be obvious to those skilled in the art that various other changes and modifications can be made without departing from the spirit and scope of the invention. It is therefore intended to cover in the appended claims all such changes and modifications within the scope of this invention.

What is claimed is:

1. An absorbent article for positioning in an undergarment to absorb body exudates, the absorbent article comprising:
   a main body portion comprising an absorbent assembly capable of absorbing body fluids, said main body portion having a body side, a garment side opposite of said body side, longitudinal edges, transverse edges, a first transverse end, a second transverse end, a transverse center disposed between said first transverse end and said second transverse end, a principal longitudinal centerline, and a principal transverse centerline which divides said main body portion into a first half and a second half; and
   a pad securement member joined to said garment side of said main body portion for securing said main body portion to the undergarment, said pad securement member comprising
      a first hook fastening material positioned in said first half of said main body portion, and
      a second hook fastening material positioned in said second half of said main body portion,
   said first hook fastening material and said second hook fastening material each comprising an oriented hook fastening material comprising
      (i) a substrate, and
      (ii) a plurality of engaging elements joined to said substrate, at least a majority of said engaging elements being generally oriented in a direction which determines the direction of orientation each hook fastening material,
   wherein said first hook fastening material and said second fastening material are generally oriented in a direction having a vector component perpendicular to said principal transverse centerline.

2. The absorbent article of claim 1 wherein said first hook fastening material and said second hook fastening material are each oriented in a direction substantially perpendicular to said principal transverse centerline.

3. The absorbent article of claim 2 wherein said first hook fastening material is oriented in a direction substantially opposite the direction of orientation of said second hook fastening material.

4. The absorbent article of claim 3 wherein said first hook fastening material and said second hook fastening material are oriented toward said principal transverse centerline.

5. The absorbent article of claim 4 wherein less than the entire surface area of said first half of said garment side comprises said first hook fastening material and wherein less than the entire surface area of said second half of said garment side comprises said second hook fastening material.

6. The absorbent article of claim 5 wherein said first hook fastening material is positioned in said first transverse end, and said second hook fastening material is positioned in said second transverse end.

7. The absorbent article of claim 6 wherein said pad securement member additionally comprises a layer of pressure-sensitive adhesive positioned in said transverse center.

8. The absorbent article of claim 6 wherein said main body portion additionally has a first longitudinal end, a second longitudinal end, and a longitudinal center between said first longitudinal end and said second longitudinal end, and wherein said pad securement member additionally comprises
   a third hook fastening material joined to said garment side of said main body portion in said first longitudinal end, and
   a fourth hook fastening material joined to said garment side of said main body portion in said second longitudinal end,
   wherein said third hook fastening material and said fourth hook fastening material each comprise an oriented hook fastening material, said third hook fastening material and said fourth hook fastening material being generally oriented in a direction having a vector component parallel to said principal transverse centerline.

9. The absorbent article of claim 8 wherein said third hook fastening material is oriented in a direction substantially opposite the direction of orientation of said fourth hook fastening material.

10. The absorbent article of claim 9 wherein said third hook fastening material and said fourth hook fastening material are oriented toward said principal longitudinal centerline.

11. The absorbent article of claim 1 additionally comprising a pair of flaps, each of said flaps being joined to said main body portion at a line of juncture, said flaps being disposed to fold around the edges of the undergarment.

12. The absorbent article of claim 11 wherein each said flap comprises a flap securement member for joining said flaps to the undergarment, said flap securement members each comprising an oriented hook fastening material comprising a substrate and a plurality of engaging elements joined to said substrate, at least a majority of said engaging elements being oriented in a direction which determines the direction of orientation of each said flap securement member, wherein each said flap securement member is oriented in a direction having a vector component perpendicular to said principal longitudinal centerline.

13. The absorbent article of claim 9 wherein one of said flap securement members is oriented toward said principal longitudinal centerline in a direction substantially opposite the direction of orientation of said flap securement member on the other flap.

14. The absorbent article of claim 13 wherein said flaps each comprise a separate material joined to said main body portion.

15. The absorbent article of claim 13 wherein each of said flaps are integral with said main body portion such that said line of juncture is along said longitudinal edge of said main body portion.

16. The absorbent article of claim 1 wherein said engaging elements of each said oriented hook fastening material are substantially all oriented in the same direction.

17. The absorbent article of claim 1 wherein said engaging elements comprise prongs.

18. The absorbent article of claim 17 wherein said main body portion comprises a topsheet, a backsheet joined with said topsheet, and an absorbent core positioned between said topsheet and said backsheet, and wherein said substrate of said oriented hook fastening material comprises said backsheet.

19. An absorbent article for positioning in an undergarment to absorb body exudates, the absorbent article comprising:
   a main body portion comprising an absorbent assembly capable of absorbing fluids, said main body portion having a body side, a garment side opposite of said body side, longitudinal edges, transverse edges, a first transverse end, a second transverse end, a transverse center between said first transverse end and said second transverse end, a first longitudinal end, a second longitudinal end, a longitudinal center between said first longitudinal end and said second longitudinal end, a principle transverse centerline which divides said main body portion into a first half and second half, and a principle longitudinal centerline which further divides said main body portion into a first quarter, a second quarter, a third quarter, and a fourth quarter; and
   a pad securement member joined to said garment side of said main body portion for securing said main body portion to the undergarment, said pad securement member comprising:
   a first hook fastening material positioned in said first quarter of said main body portion,
   a second hook fastening material positioned in said second quarter of said main body portion,
   a third hook fastening material positioned in said third quarter of said main body portion, and
   a fourth hook fastening material positioned in said fourth quarter of said main body portion,
   said first hook fastening material, said second hook fastening material, said third hook fastening material, and said fourth hook fastening material, each comprising an oriented hook fastening material comprising
     (i) a substrate, and
     (ii) a plurality of engaging elements joined to said substrate, at least a majority of said engaging elements being generally oriented in a direction which determines the direction of orientation of each hook fastening material,
   wherein said first hook fastening material, said second hook fastening material, said third hook fastening material, and said fourth hook fastening material are generally oriented in a direction having a vector component perpendicular to said transverse centerline and a vector component perpendicular to said longitudinal centerline.

20. The absorbent article of claim 19 wherein said first hook fastening material is oriented in a direction substantially opposite the direction of orientation of said third hook fastening material, and wherein said second hook fastening material is oriented in a direction substantially opposite the direction of orientation of said fourth hook fastening material.

21. The absorbent article of claim 20 wherein less than the entire surface area of said first quarter comprises said first hook fastening material, wherein less than the entire surface area of said second quarter comprises said second hook fastening material, wherein less than the entire surface area of said third quarter comprises said third hook fastening material, and wherein less than the entire surface area of said fourth quarter comprises said fourth hook fastening material.

22. The absorbent article of claim 21 wherein said first hook fastening material is positioned in said first transverse end and said first longitudinal end, said second hook fastening material is positioned in said first transverse end and said second longitudinal end, said third hook fastening material is positioned in said second transverse end and said second longitudinal end, and said fourth hook fastening material is positioned in said second transverse end and said first longitudinal end.

23. The absorbent article of claim 22 wherein said pad securement member additionally comprises a layer of pressure-sensitive adhesive positioned in said transverse center of said main body portion.

24. The absorbent article of claim 22 wherein said pad securement member additionally comprises
   a fifth hook fastening material joined to said garment side of said main body portion in said first longitudinal end and said transverse center, and a sixth hook fastening material joined to said garment side of said main body portion in said second longitudinal end and said transverse center, said fifth hook fastening material and said sixth hook fastening material each comprising an oriented hook fastening material, wherein said fifth hook fastening material and said sixth hook fastening material are generally oriented in a direction having a vector component perpendicular to said principal longitudinal centerline, and wherein said fifth hook fastening material is oriented in a direction substantially opposite the direction of orientation of said sixth hook fastening material.

25. The absorbent article of claim 24 wherein said pad securement member additionally comprises a seventh hook fastening material joined to said garment side of said main body portion in said first transverse end and said longitudinal center, and an eighth oriented hook fastening material joined to said garment side of said main body portion in said second transverse end and said longitudinal center, said seventh hook fastening material and said eighth hook fastening material each comprising an oriented hook fastening material, said seventh hook fastening material and said eighth hook fastening material being generally oriented in a direction having a vector component perpendicular to said principle transverse centerline, and wherein said seventh hook fastening material is oriented in a direction substantially opposite the direction of orientation of said eighth hook fastening material.

26. The absorbent article of claim 25 wherein pad securement member additionally comprises a layer of pressure-sensitive adhesive positioned in said transverse center and said longitudinal center.

27. The absorbent article of claim 22 wherein said pad securement member additionally comprises a fifth hook fastening material joined to said garment side of said main body portion in said first transverse end and said longitudinal center, and a sixth hook fastening material joined to said garment side of said main body portion in said second transverse end and said longitudinal center, said fifth hook fastening material and said sixth hook fastening material each comprising an oriented hook fastening material, said fifth hook fastening material and said sixth hook fastening material being generally oriented in a direction having a vector component perpendicular to said principal transverse centerline, and wherein said fifth hook fastening material is oriented in a direction substantially opposite the direction of orientation of said sixth hook fastening material.

28. The absorbent article of claim 27 wherein said pad securement member additionally comprises a layer of pressure sensitive adhesive positioned in said transverse center.

29. The absorbent article of claim 19 wherein said engaging elements of each said oriented hook fastening material are substantially all oriented in the same direction.

30. The absorbent article of claim 19 wherein said engaging elements each comprise prongs.

31. The absorbent article of claim 30 wherein said main body portion comprises a topsheet, a backsheet joined with said topsheet, and an absorbent core disposed between said topsheet and said backsheet, and wherein said substrate of each said oriented hook fastening material comprises said backsheet.

32. An absorbent article for positioning in an undergarment to absorb body exudates, the absorbent article comprising:

a main body portion comprising an absorbent assembly capable of absorbing fluids, said main body portion having a body side, a garment side opposite of said body side, longitudinal edges, transverse edges, a principle transverse centerline and a principle longitudinal centerline; and a pair of flaps, each of said flaps being joined to said main body portion at a line of juncture, said flaps being disposed to fold around the edges of the undergarment, each of said flaps having a flap body side and a flap garment side, each of said flaps comprising a flap securement member joined to said flap garment side of securing member comprising an oriented hook fastening material, said oriented hook fastening material comprising (i) a substrate, and (ii) a plurality of engaging elements joined to said substrate, a majority of said engaging elements of each oriented hook fastening material being generally oriented in a direction which determines the direction of orientation of each flap securement member, wherein each said flap securement member is generally oriented in a direction having a vector component perpendicular to said principal longitudinal centerline.

33. The absorbent article of claim 32 wherein said flap securement member on one of said flaps is oriented in a direction substantially opposite the direction of orientation of said flap securement member of the other of said flaps.

34. The absorbent article of claim 33 wherein said main body portion additionally comprises a pad securement member joined to said garment side of said main body portion for securing said main body portion to the undergarment.

35. The absorbent article of claim 34 wherein said pad securement member comprises a layer of pressure sensitive adhesive.

36. The absorbent article of claim 34 wherein said pad securement member comprises an oriented hook fastening material.

37. The absorbent article of claim 33 wherein each of said flaps comprises a separate material joined to said main body portion.

38. The absorbent article of claim 34 wherein each of said flaps are integral with said main body portion such that said line of juncture is along said longitudinal edge of said main body portion.

* * * * *

UNITED STATES PATENT AND TRADEMARK OFFICE
CERTIFICATE OF CORRECTION

PATENT NO. : 5,300,058

DATED : April 5, 1994

INVENTOR(S) : DAVID J. K. GOULAIT, et al.

It is certified that error appears in the above-identified patent and that said Letters Patent is hereby corrected as shown below:

Column 4, line 12, "fastenings" should read --fastening--.

Column 6, line 46, "i s," should read --is,--.

Column 8, line 63, "A. The To sheet" should read --A. The Topsheet--.

Column 9, line 36, "patent application" should read --Patent Application--.

Column 9, line 48, "patent application" should read --Patent Application--.

Column 9, line 52, "patent application" should read --Patent Application--.

Column 9, lines 57 & 58, "patent application" should read --Patent Application--.

Column 9, line 62, "et al . on" should read --et al. on--.

Column 9, line 68, "patent application" should read --Patent Application--.

Column 10, lines 3 & 4, "patent application" should read --Patent Application--.

Column 10, line 6, "patent applica-" should read --Patent Applica----.

Column 15, line 50, "patent application" should read --Patent Application--.

Column 15, line 65, "patent application" should read --Patent Application--.

Column 16, line 13, "patent application" should read --Patent Application--.

UNITED STATES PATENT AND TRADEMARK OFFICE
CERTIFICATE OF CORRECTION

PATENT NO. : 5,300,058

DATED : April 5, 1994

INVENTOR(S) : DAVID J. K. GOULAIT, et al.

It is certified that error appears in the above-identified patent and that said Letters Patent is hereby corrected as shown below:

Column 21, line 60, "patent application" should read --Patent Application--.

Column 21, line 63, "patent application" should read --Patent Application--.

Column 23, line 17, "patent application" should read --Patent Application--.

Column 17, line 33, "patent application" should read --Patent Application--.

Signed and Sealed this

Twenty-ninth Day of July, 1997

Attest:

BRUCE LEHMAN

Attesting Officer

Commissioner of Patents and Trademarks